United States Patent
Mou et al.

(10) Patent No.: US 11,733,143 B2
(45) Date of Patent: Aug. 22, 2023

(54) EXTERNAL GAS DETECTING DEVICE

(71) Applicant: Microjet Technology Co., Ltd., Hsinchu (TW)

(72) Inventors: Hao-Jan Mou, Hsinchu (TW); Ching-Sung Lin, Hsinchu (TW); Chin-Chuan Wu, Hsinchu (TW); Yung-Lung Han, Hsinchu (TW); Chi-Feng Huang, Hsinchu (TW); Chang-Yen Tsai, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 223 days.

(21) Appl. No.: 17/087,248

(22) Filed: Nov. 2, 2020

(65) Prior Publication Data

US 2021/0172850 A1    Jun. 10, 2021

(30) Foreign Application Priority Data

Dec. 6, 2019 (TW) ................................ 108144822
Jan. 16, 2020 (TW) ................................ 109101602

(51) Int. Cl.
*G01N 15/06* (2006.01)
*G01N 33/00* (2006.01)
*G01N 15/02* (2006.01)
*G01N 1/24* (2006.01)

(52) U.S. Cl.
CPC ............ *G01N 15/06* (2013.01); *G01N 1/24* (2013.01); *G01N 15/0205* (2013.01); *G01N 33/0047* (2013.01); *G01N 2015/0693* (2013.01)

(58) Field of Classification Search
None
See application file for complete search history.

(56) References Cited

U.S. PATENT DOCUMENTS

| 9,983,189 B2* | 5/2018 | Perreault | F02C 3/00 |
|---|---|---|---|
| 11,169,069 B2* | 11/2021 | Mou | G01N 15/1459 |
| 2006/0114115 A1* | 6/2006 | Smith | G01N 33/0047 |
| | | | 340/634 |
| 2007/0086008 A1* | 4/2007 | Schweighardt | G01N 15/06 |
| | | | 356/337 |
| 2009/0116536 A1* | 5/2009 | Amato | G01K 3/14 |
| | | | 374/E1.001 |

(Continued)

FOREIGN PATENT DOCUMENTS

| TW | M497302 U | 3/2015 |
|---|---|---|
| TW | M574228 U | 2/2019 |
| TW | M582134 U | 8/2019 |

*Primary Examiner* — Dominic J Bologna
*Assistant Examiner* — Jarreas C Underwood
(74) *Attorney, Agent, or Firm* — Birch, Stewart, Kolasch & Birch, LLP

(57) ABSTRACT

An external gas detecting device is provided. The external gas detecting device includes a casing, a gas detection module and an external connector. The gas detection module is disposed in the casing and detects a gas transported into the casing to generate a gas information. The external connector is connected to and disposed on the casing. The external connector is used to be connected to an external power supply so as to enable the gas detection module, and is used to transmit the gas information so as to achieve the outward transmission of the gas information.

20 Claims, 28 Drawing Sheets

(56) References Cited

U.S. PATENT DOCUMENTS

| | | | |
|---|---|---|---|
| 2013/0211732 A1* | 8/2013 | Chuang | G01N 33/0059 |
| | | | 73/31.05 |
| 2016/0209382 A1* | 7/2016 | Shalom | G01N 1/2273 |
| 2019/0178775 A1* | 6/2019 | Feng | G01N 1/24 |
| 2019/0187035 A1* | 6/2019 | Mou | G01N 15/06 |
| 2020/0292437 A1* | 9/2020 | Mou | F04F 7/00 |
| 2020/0292438 A1* | 9/2020 | Mou | G01N 15/02 |
| 2021/0053679 A1* | 2/2021 | Johannesson | B64U 20/40 |

* cited by examiner

EXTERNAL GAS DETECTING DEVICE

FIELD OF THE INVENTION

The present disclosure relates to an external gas detecting device, and more particularly to an external gas detecting device with extremely thin profile.

BACKGROUND OF THE INVENTION

Suspension particles are solid particles or droplets within the gas. Since the suspension particles are extremely fine, it is often that the suspension particles are inhaled into the lung by passing through the nose hair inside the nasal cavity of human's body. As a result, inflammation of the lungs, asthma or cardiovascular diseases are caused. Furthermore, if the suspension particles are attached with other pollutants, it will be more harmful to the respiratory system of human's body. Recently, the problem of the gas pollution is getting worse, especially, the concentration data of fine suspended particles, e.g., PM2.5, is often too high. Therefore, the detection of the concentration of the suspension particles is getting more attention. However, since the gas flows unstably owing to the wind direction and air volume, and the conventional air quality monitoring stations used for detecting the suspension particles are fixedly disposed at certain locations, people cannot check the concentration of the suspension particles in the surrounding environment.

Moreover, people pay more attention to the quality of the air around their lives. For example, carbon monoxide, carbon dioxide, volatile organic compounds (VOC), PM2.5, nitric oxide, sulfur monoxide and even the suspended particles contained in the air are exposed in the environment to affect the human health, and even endanger the life seriously. Therefore, the quality of environmental air has attracted the attention of various countries. How to detect the air quality and avoid the harm from the area with poor air quality is a problem that urgently needs to be solved.

In order to confirm the quality of the air, it is feasible to use a gas sensor to detect the air surrounding in the environment. If the detection information is provided in real time to warn the people in the environment, it is helpful of avoiding the harm and facilitates the people to escape the hazard immediately. Thus, it prevents the hazardous gas exposed in the environment from affecting the human health and causing the harm. Therefore, it is a very good application to use a gas sensor to detect the air in the surrounding environment.

On the other hand, it is common that the portable devices are carried by the modern people when they go out. It is taken seriously that the gas detection module is embedded in the portable device for detecting the air in the surrounding environment. In particular, the current development trend of portable devices is light and thin Therefore, how to make the gas detection module thinner and install it in the portable device is an important subject developed in the present disclosure. There is a need of providing an external gas detecting device with thin profile and easy to be carried, so that the user can detect the concentration of the suspension particles and the air quality in the surrounding environment anytime and anywhere.

SUMMARY OF THE INVENTION

An object of the present disclosure provides an external gas detecting device. With the gas detection module embedded in the external gas detecting device, the air quality in the surrounding environment around the user is detected anytime, the information of the air quality is transmitted to the external transmission device in real time, and an alarm of the information of the gas detection is obtained.

In accordance with an aspect of the present disclosure, an external gas detecting device is provided. The external gas detecting device includes a casing, a gas detection module and an external connector. The gas detection module is disposed in the casing and detects a gas transported into the casing to generate a gas information. The external connector is connected to and disposed on the casing. The external connector is used to be connected to an external power supply so as to enable the gas detection module, and is used to transmit the gas information so as to achieve the outward transmission of the gas information.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1A:
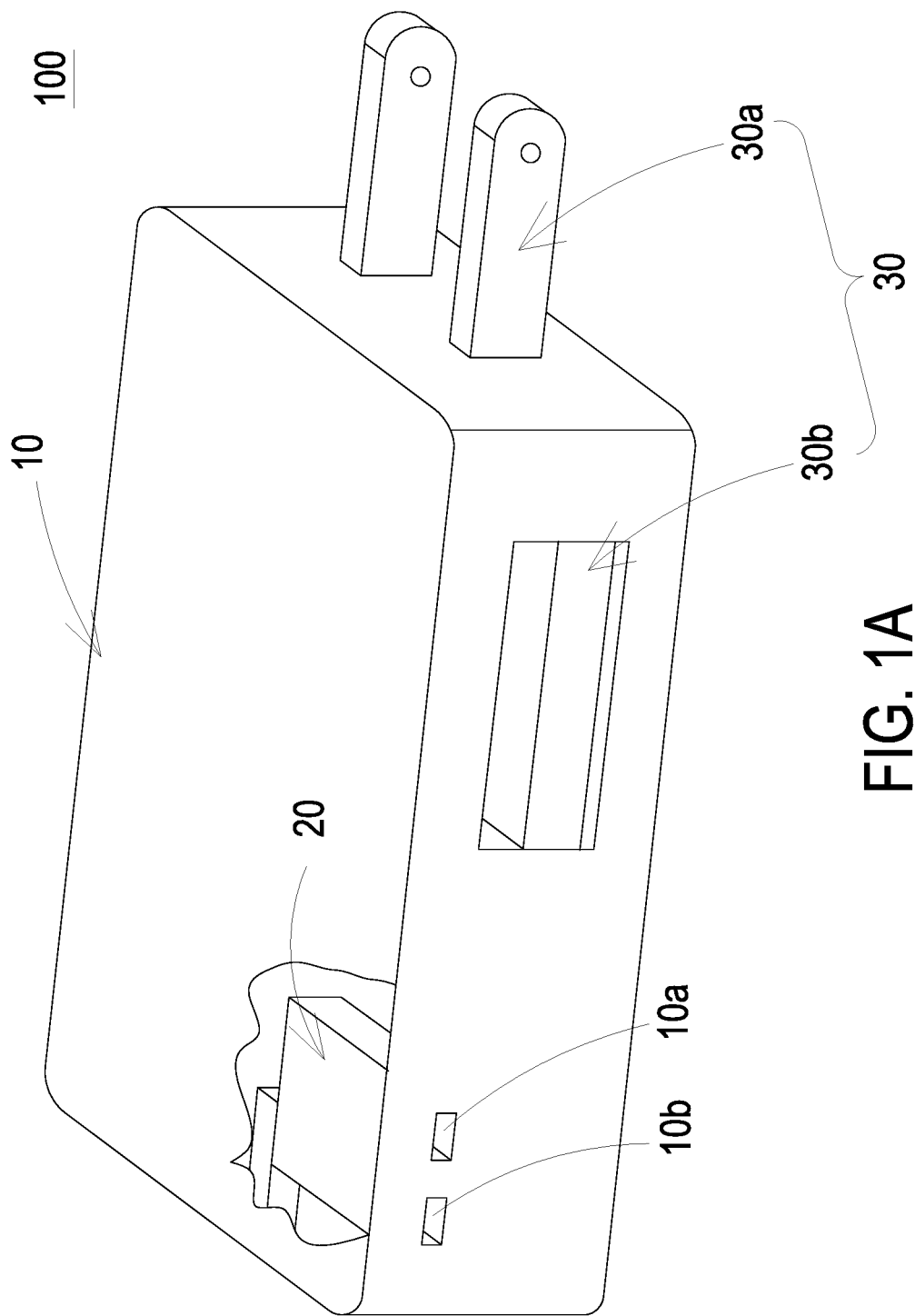
FIG. 1A shows a schematic exterior view illustrating an external gas detecting device according to an embodiment of the present disclosure.

Please refer to FIGS. 1A, 1B, 1C, 1D, 1E, 2A, 2B, 2C and 12. The present disclosure provides an external gas detecting device 100. The external gas detecting device 100 includes a casing 10, a gas detection module 20 and an external connector 30. The casing 10 includes a gas-inlet channel 10a and a gas-outlet channel 10b. The gas detection module 20 is disposed in the casing 10 and transports the gas outside the casing 10 into the casing 10 through the gas-inlet channel 10a, so as to output a gas information. After the gas is detected, the gas detection module 20 transports the detected gas out of the casing 10. The external connector 30 is connected to and disposed on the casing 10, and is connected to an external power supply so as to enable the gas detection module 20 to operate and achieve the outward transmission of the gas information. The external connector 30 is one selected from the group consisting of a USB connector, a mini USB connector, a Micro USB connector, a USB Type C connector, an AC adapter, a DC power adapter, a power connector, a terminal connector and combination thereof. In the embodiment, as shown in FIG. 1A, the external connector 30 is combination of an AC adapter 30a in a plug form and a USB connector 30b in a receptacle form. The AC adapter 30a can be plugged in an external receptacle (not shown) and be electrically coupled therewith so as to achieve the connection between the external power supply and the external gas detecting device 100. Consequently, the gas detection module 20 is enabled to operate, detect the gas and generate the gas information. Thereafter, by connecting the USB connector 30b to an external connection device 50, such as mobile device, the outward transmission of the gas information is achieved.

Figure 1B:
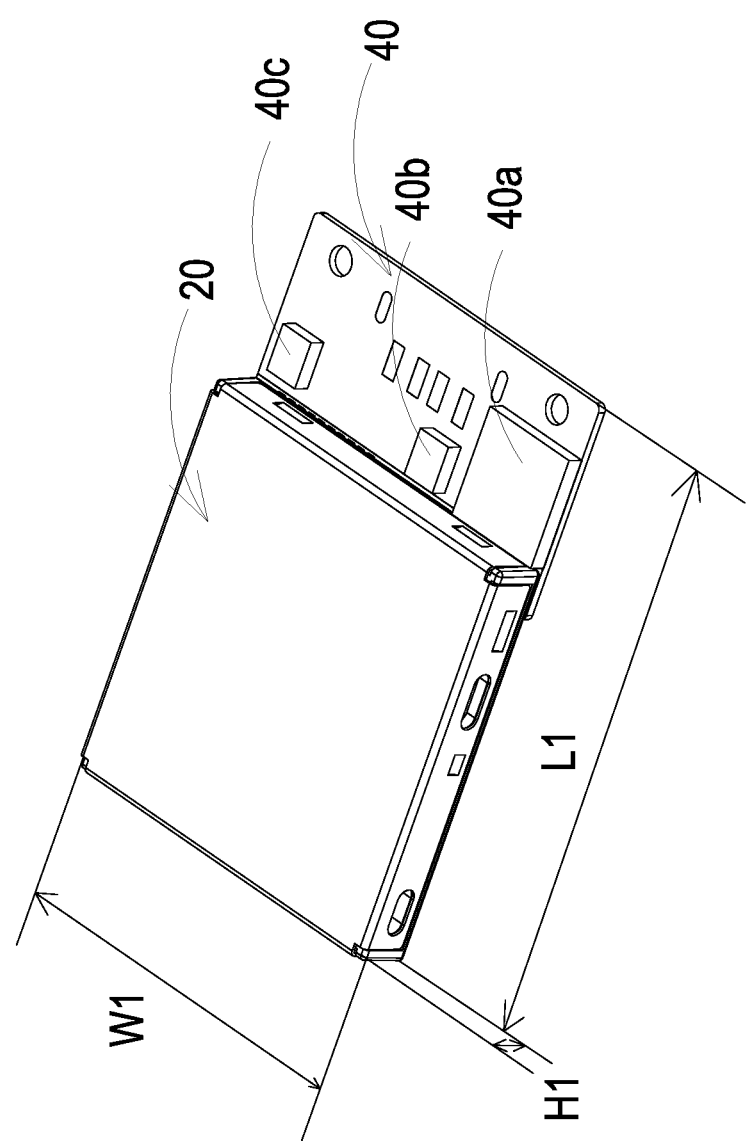
FIG. 1B shows a schematic exterior view illustrating a gas detecting and transmitting module of an external gas detecting device according to another embodiment of the present disclosure.
Figure 1C:
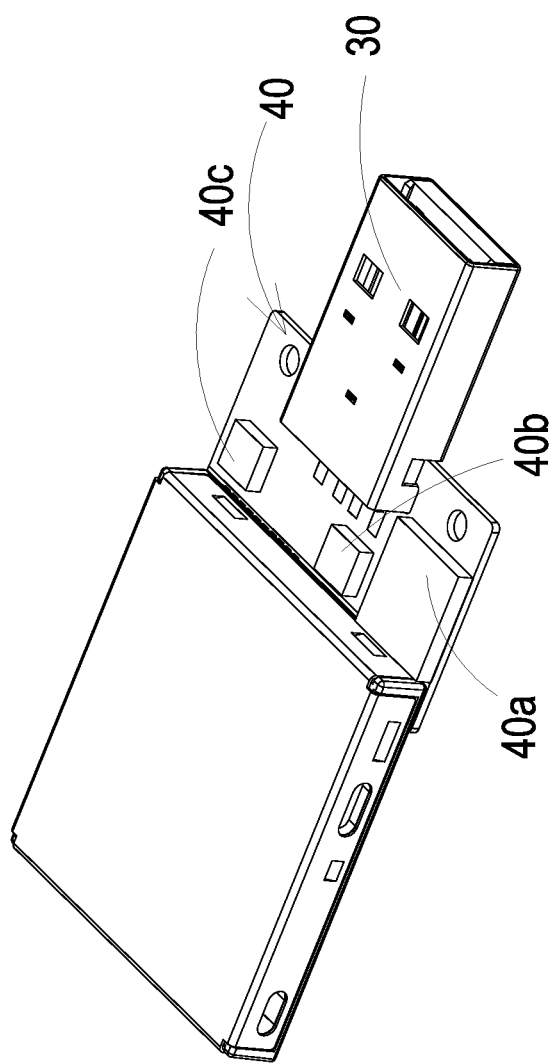
FIG. 1C shows a schematic exterior view illustrating the assembly of a gas detecting and transmitting module and an external connector of an external gas detecting device according to another embodiment of the present disclosure.
Figure 1D:
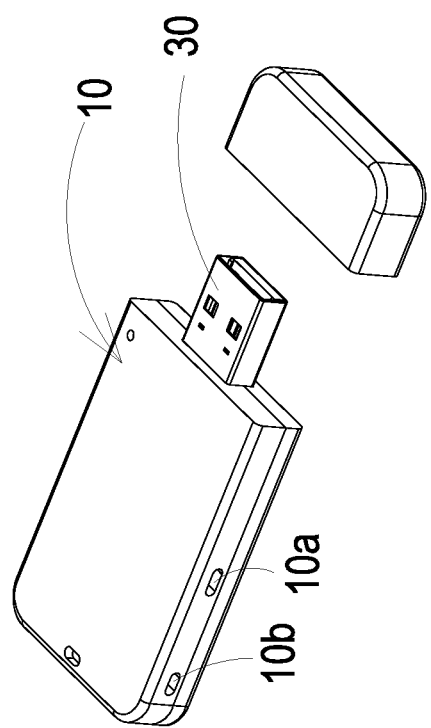
FIG. 1D shows a schematic exterior view illustrating the assembly of a gas detecting and transmitting module, an external connector and a casing of an external gas detecting device according to another embodiment of the present disclosure.
Figure 1E:
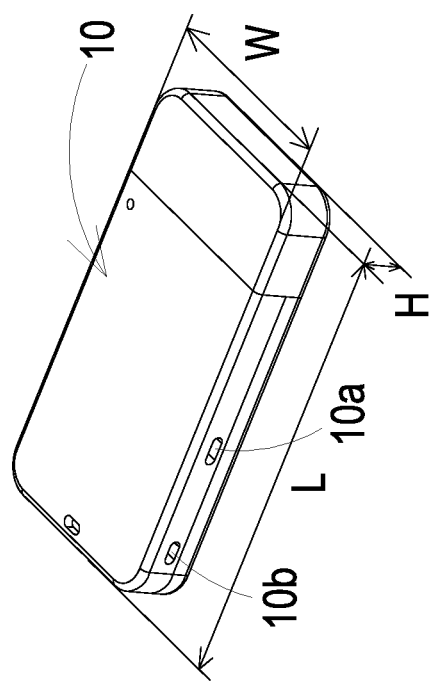
FIG. 1E shows a schematic exterior view illustrating an external gas detecting device according to another embodiment of the present disclosure.
Figure 12:
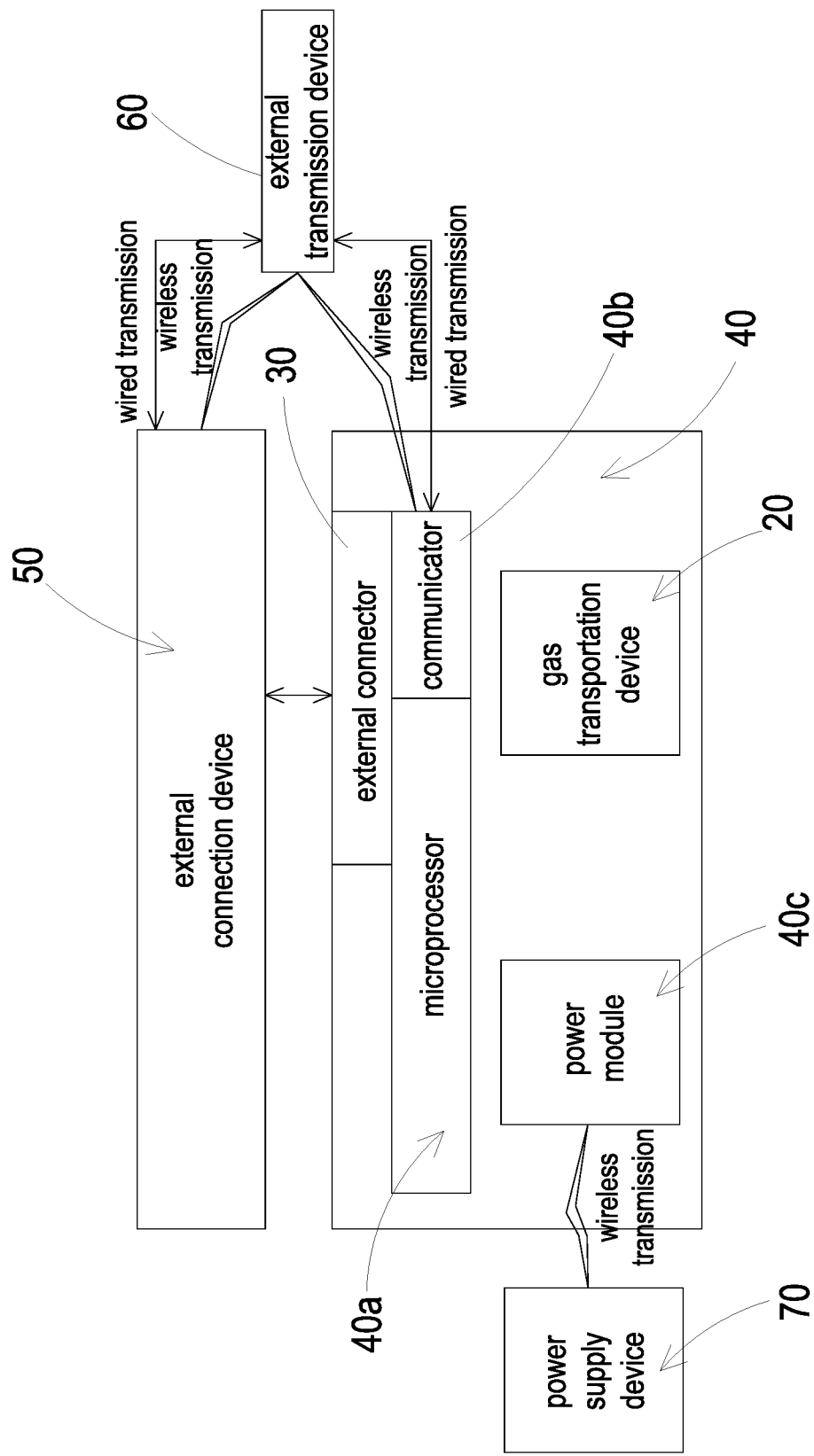
FIG. 12 is a block diagram showing the relationship between the controlling circuit unit and the related arrangement of the external gas detecting device according to the embodiment of the present disclosure.

As shown in FIGS. 1B and 12, the external gas detecting device 100 further includes a controlling circuit unit 40. A microprocessor 40a, a communicator 40b and a power module 40c are disposed on and electrically coupled with the controlling circuit unit 40. To make the external gas detecting device 100 meet the trend of lightweight-miniaturized structure and portability, the gas detection module 20 of the present disclosure is assembled with the controlling circuit unit 40 after the thickness thereof is decreased, so as to form a gas detecting and transmitting module 100A. The gas detecting and transmitting module 100A has a length L1 ranging between 35 mm and 55 mm, a width W1 ranging between 10 mm and 35 mm, and a thickness H1 ranging between 1 mm and 7.5 mm. The sizes of the gas detecting and transmitting module 100A benefits the assembly shown in FIG. 1B. Thereafter, as shown in FIG. 1C, the gas detecting and transmitting module 100A is further assembled with and electrically connected to the external connector 30. The casing 10 covers the gas detecting and transmitting module 100A and the external connector 30 so as to protect them, and the external connector 30 is exposed to achieve the electrical connection, as shown in FIG. 1D. In addition, the casing 10 includes the gas-inlet channel 10a and the gas-outlet channel 10b. Therefore, as shown in FIG. 12, the power module 40c can receive an electric energy through a power supply device 70 via a wireless transmission technology for storing the electric energy. The microprocessor 40a enables the gas detection module 20 to detect and operate by controlling a driving signal of the gas detection module 20. The gas detection module 20 is disposed in the casing 10 so as to transport the gas into the interior of the casing 10 through the gas-inlet channel 10a and obtain the gas information, and then transport the detected gas out of the casing 10 through the gas-outlet channel 10b. The microprocessor 40a converts the gas information of the gas detection module 20 into a detection data. The communicator 40b is used to receive the detection data outputted by the microprocessor 40a, so that the detection data is externally transmitted to an external transmission device 60 through the communication transmission for storing. Furthermore, it results that the external transmission device 60 generates a gas detection information and an alarm based on the detection data. In other embodiments, the external connector 30 is connected to the external connection device 50, such as mobile device, to achieve the connection between the external power supply and the external gas detecting device 100 and enable the gas detection module 20 to operate. The gas detection module 20 detects the gas outside the casing 10 to generate the gas information. The microprocessor 40a converts the gas information of the gas detection module 20 to a detection data for storing. By the connection between the external connector 30 and the external connection device 50, the detection data is transmitted to the external connection device 50 for processing and application. Furthermore, the gas detection data is further transmitted outwardly by the external connection device 50 through the communication transmission to the external transmission device 60 for storing. Furthermore, it results that the external transmission device 60 generates the gas detection information and the alarm based on the detection data.

Preferably but not exclusively, the above-mentioned external transmission device 60 is one selected from the group consisting of a cloud system, a portable device and a computer system. Preferably but not exclusively, the above-mentioned communication transmission is the wired communication transmission, such as USB transmission. Preferably but not exclusively, the communication transmission is the wireless communication transmission, such as Wi-Fi transmission, Bluetooth transmission, a radio frequency identification transmission or a near field communication transmission. The external gas detecting device 100 including the above-mentioned features has a length L ranging between 45 mm and 70 mm, a width W ranging between 25 mm and 42 mm, and a thickness H ranging between 7 mm and 13 mm. It benefits the construction as shown in FIGS. 1A, 1B, 1C, 1D and 1E which meet the requirement of the design with lightweight-miniaturized structure and portability.

Figure 2A:
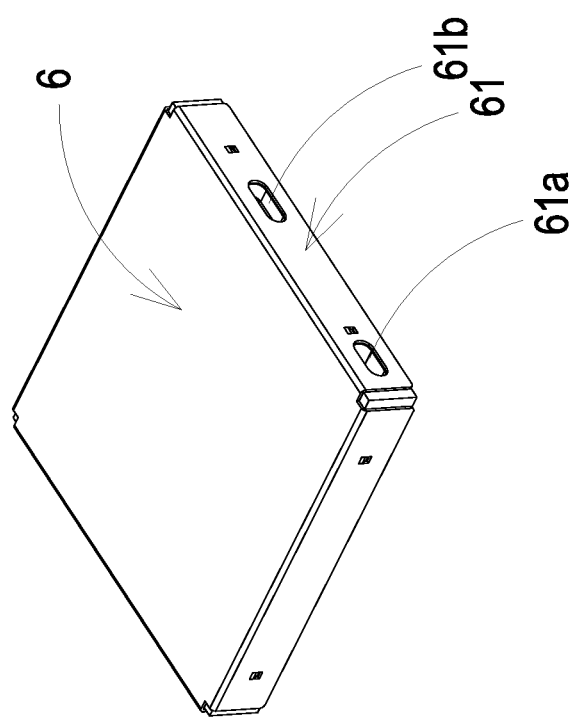
FIG. 2A is a schematic exterior view illustrating a gas detection module according to an embodiment of the present disclosure.
Figure 2B:
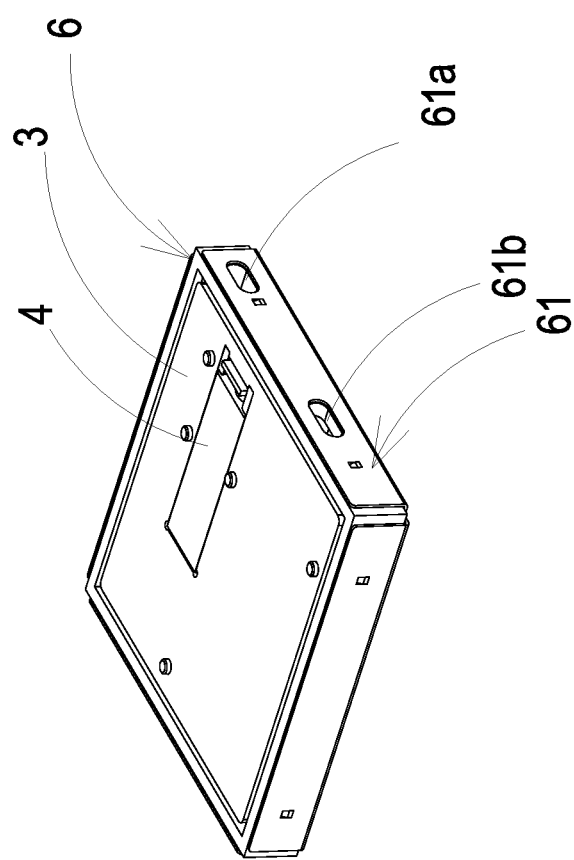
FIG. 2B is a schematic exterior view illustrating the gas detection module according to the embodiment of the present disclosure and taken from another perspective angle.
Figure 2C:
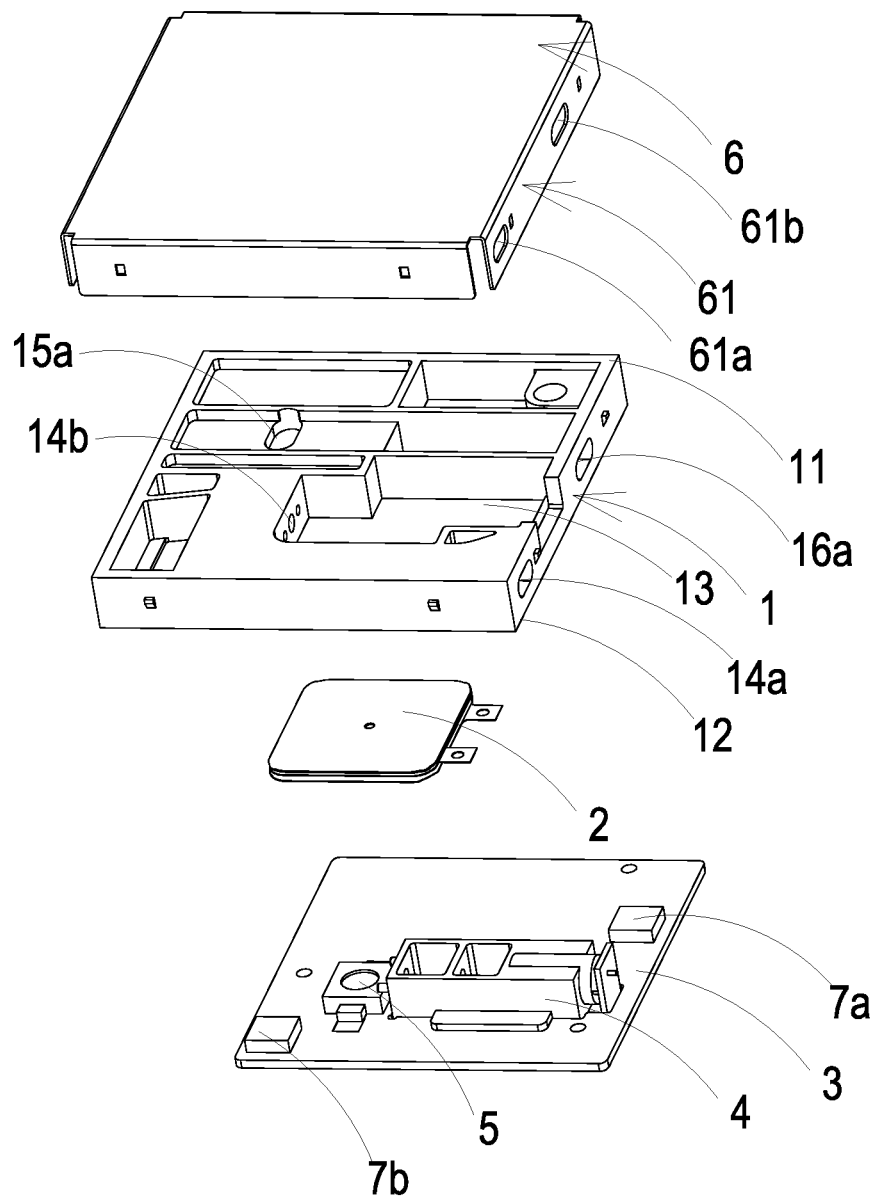
FIG. 2C is a schematic exploded view illustrating the gas detection module of the present disclosure.

Please refer to FIGS. 2A to 2C. The present disclosure provides a gas detection module 20 including a base 1, a piezoelectric actuator 2, a driving circuit board 3, a laser component 4, a particle sensor 5 and an outer cover 6. In the embodiment, the driving circuit board 3 covers and is attached to the second surface 12 of the base 1, and the laser component 4 is positioned and disposed on the driving circuit board 3, and is electrically connected to the driving circuit board 3. The particle sensor 5 is positioned and disposed on the driving circuit board 3, and is electrically connected to the driving circuit board 3. The outer cover 6 covers the base 1 and is attached to the first surface 11 of the base 1. Moreover, the outer cover 6 includes a side plate 61. The side plate 61 includes an inlet opening 61a and an outlet opening 61b. When the gas detection module 20 is disposed in the casing 10, the inlet opening 61a is spatially corresponding to the gas-inlet channel 10a of the casing 10, and the outlet opening 61b is spatially corresponding to the gas-outlet channel 10b of the casing 10.

Figure 3A:
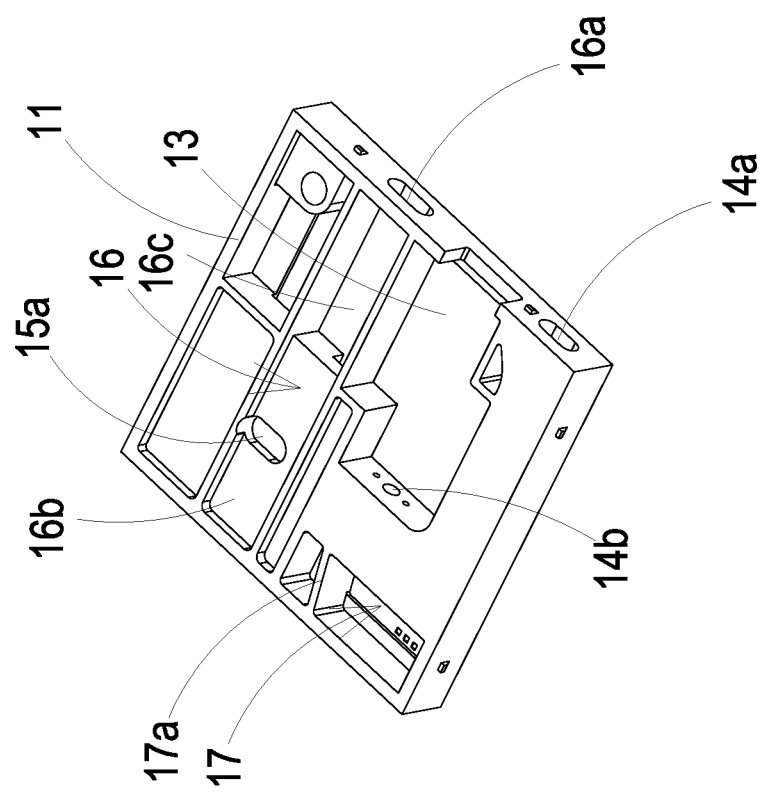
FIG. 3A is a schematic perspective view illustrating a base of the gas detection module of the present disclosure.
Figure 3B:
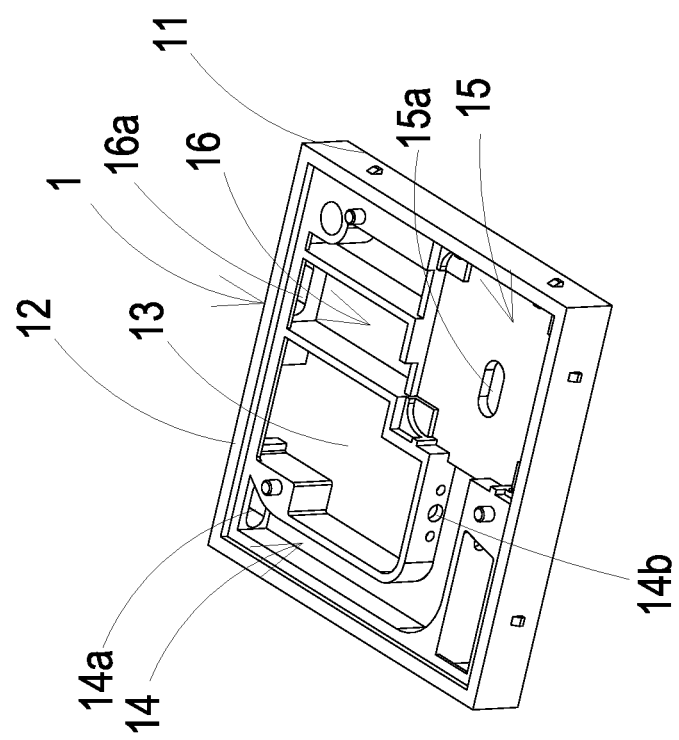
FIG. 3B is a schematic perspective view illustrating the base of the gas detection module of the present disclosure and taken from another perspective angle.

Please refer to FIG. 3A and FIG. 3B. In the embodiment, the base 1 includes a first surface 11, a second surface 12, a laser loading region 13, a gas-inlet groove 14, a gas-guiding-component loading region 15 and a gas-outlet groove 16. The first surface 11 and the second surface 12 are two opposite surfaces. The laser loading region 13 is hollowed out from the first surface 11 to the second surface 12. The gas-inlet groove 14 is concavely formed from the second surface 12 and disposed adjacent to the laser loading region 13. The gas-inlet groove 14 includes a gas-inlet 14a and two lateral walls. The gas-inlet 14a is in fluid communication with an exterior of the base 1 and spatially corresponds to the inlet opening 61a of the outer cover 6. The two lateral walls are extended towards a transparent window 14b corresponding to the laser loading region 13. In that, the first surface 11 of the base 1 is attached and covered by the outer cover 6, and the second surface 12 of the base 1 is attached and covered by the driving circuit board 3, so that an inlet path is collaboratively defined by the gas-inlet groove 14 and the driving circuit board 3.

In the embodiment, the gas-guiding-component loading region 15 mentioned above is concavely formed from the second surface 12 and in fluid communication with the gas-inlet groove 14. A ventilation hole 15a is penetrated through a bottom surface of the gas-guiding-component loading region 15. The gas-outlet groove 16 mentioned above includes a gas-outlet 16a, and the gas-outlet 16a spatially corresponds to the outlet opening 61b of the outer cover 6. The gas-outlet groove 16 includes a first section 16b and a second section 16c. The first section 16b is hollowed out from the first surface 11 to the second surface 12 in a vertical projection area of the gas-guiding-component loading region 15 spatially corresponding thereto. The second section 16c is hollowed out from the first surface 11 to the second surface 12 in a region of the first surface 11 misaligned to the vertical projection area of the gas-guiding-component loading region 15 and extended therefrom. The first section 16b and the second section 16c are connected to form a stepped structure. Moreover, the first section 16b of the gas-outlet groove 16 is in fluid communication with the ventilation hole 15a of the gas-guiding-component loading region 15, and the second section 16c of the gas-outlet groove 16 is in fluid communication with the gas-outlet 16a. In that, the first surface 11 of the base 1 is attached and covered by the outer cover 6, and the second surface 12 of the base 1 is attached and covered by the driving circuit board 3, so that an outlet path is collaboratively defined by the gas-outlet groove 16, the outer cover 6 and the driving circuit board 3.

Figure 4:
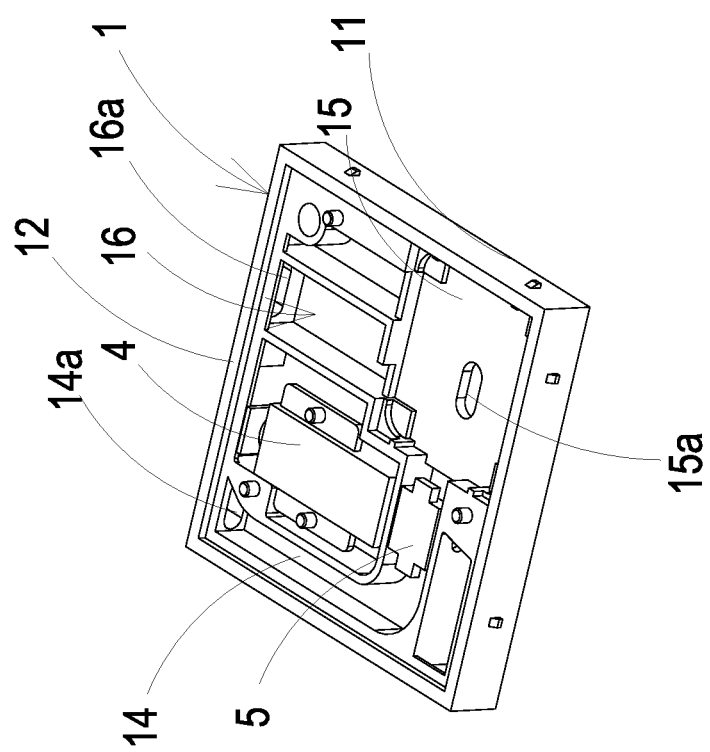
FIG. 4 is a schematic perspective view illustrating a laser component and a particle sensor accommodated in the base of the gas detection module of the present disclosure.

FIG. 4 is a schematic perspective view illustrating a laser component and a particle sensor accommodated in the base of the gas detection module of the present disclosure. In the embodiment, the laser component 4 and the particle sensor 5 are disposed on the driving circuit board 3 and accommodated in the base 1. In order to describe the positions of the laser component 4 and the particle sensor 5 in the base 1, the driving circuit board 3 is specifically omitted in FIG. 4 to explain clearly. Please refer to FIG. 4 and FIG. 2C. The laser component 4 is accommodated in the laser loading region 13 of the base 1, and the particle sensor 5 is accommodated in the gas-inlet groove 14 of the base 1 and aligned to the laser component 4. In addition, the laser component 4 spatially corresponds to the transparent window 14b, a light beam emitted by the laser component 4 passes through the transparent window 14b and is irradiated into the gas-inlet groove 14. A light beam path emitted from the laser component 4 passes through the transparent window 14b and forms an orthogonal direction with the gas-inlet groove 14.

In the embodiment, the particle sensor 5 is disposed at an orthogonal position where the gas-inlet groove 14 intersects the light beam path of the laser component 4 in the orthogonal direction, so that suspended particles passing through the gas-inlet groove 14 and irradiated by a projecting light beam emitted from the laser component 4 are detected.

In the embodiment, a projecting light beam emitted from the laser component 4 mentioned above passes through the transparent window 14b and enters the gas-inlet groove 14, and suspended particles contained in the gas passing through the gas-inlet groove 14 is irradiated by the projecting light beam. When the suspended particles contained in the gas are irradiated to generate scattered light spots, the scattered light spots are received and calculated by the particle sensor 5 for obtaining related information about the sizes and the concentration of the suspended particles contained in the gas. In the embodiment, the particle sensor 5 is a PM2.5 sensor.

Figure 5A:
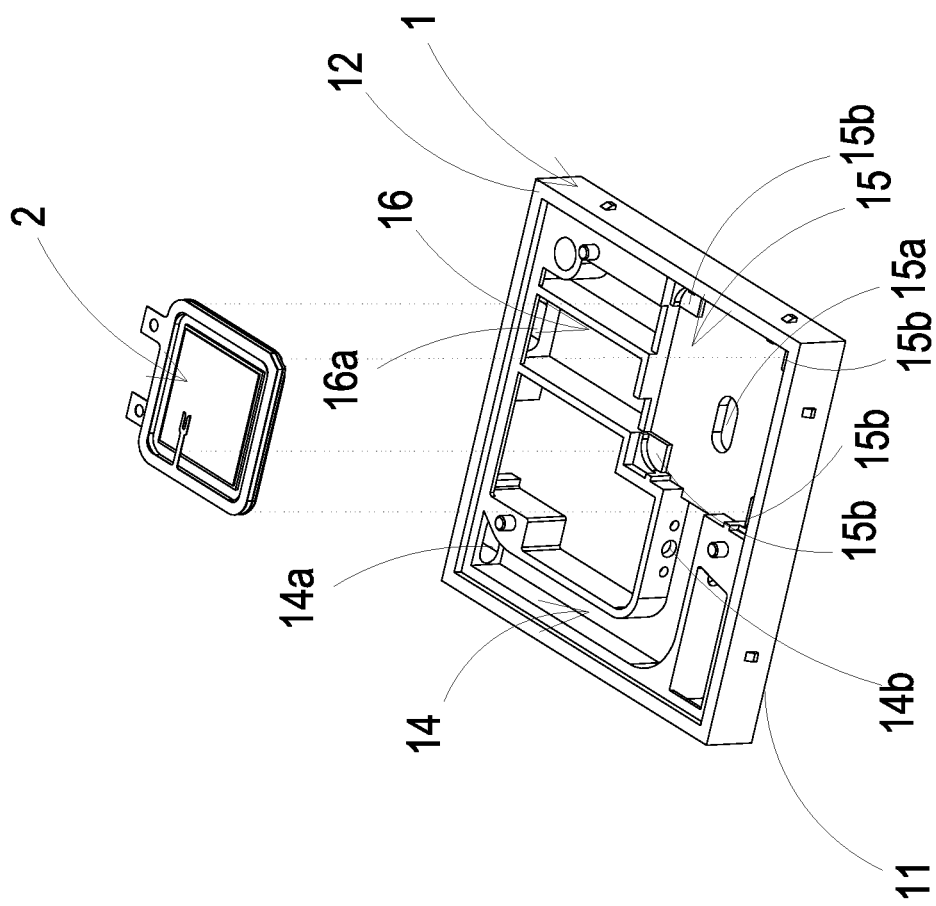
FIG. 5A is a schematic exploded view illustrating the combination of the piezoelectric actuator and the base of the gas detection module of the present disclosure.
Figure 5B:
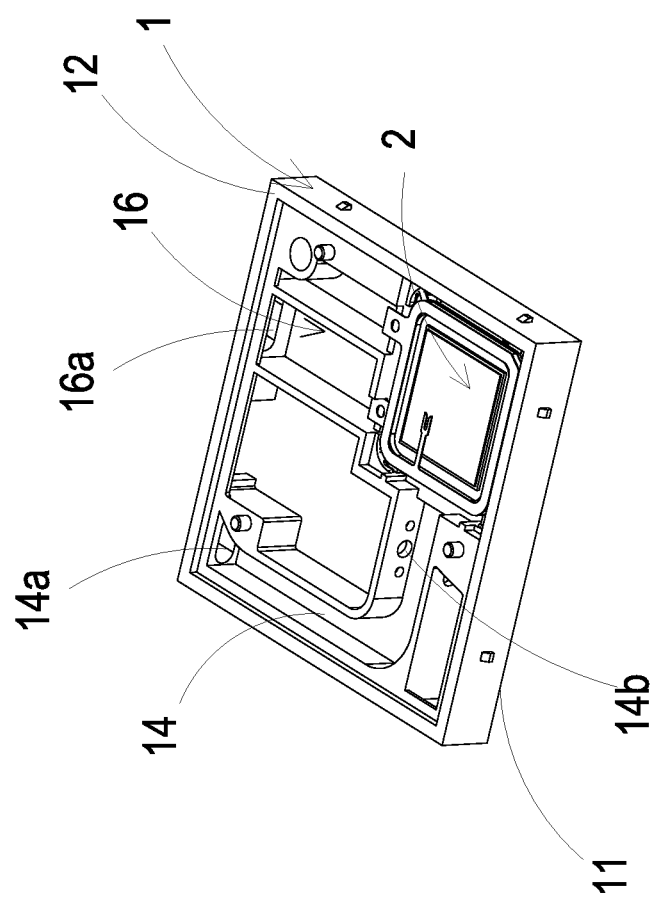
FIG. 5B is a schematic perspective view illustrating the combination of the piezoelectric actuator and the base of the gas detection module of the present disclosure.

Please refer to FIG. 5A and FIG. 5B. The piezoelectric actuator 2 mentioned above is accommodated in the gas-guiding-component loading region 15 of the base 1. Preferably but not exclusively, the gas-guiding-component loading region 15 is square and includes four positioning protrusions 15b disposed at four corners of the gas-guiding-component loading region 15, respectively. The piezoelectric actuator 2 is disposed in the gas-guiding-component loading region 15 through the four positioning protrusions 15b. In addition, the gas-guiding-component loading region 15 is in fluid communication with the gas-inlet groove 14. When the piezoelectric actuator 2 is enabled, the gas in the gas-inlet groove 14 is inhaled by the piezoelectric actuator 2, so that the gas flows into the piezoelectric actuator 2.

Furthermore, the gas is transported into the gas-outlet groove 16 through the ventilation hole 15a of the gas-guiding-component loading region 15.

Figure 6A:
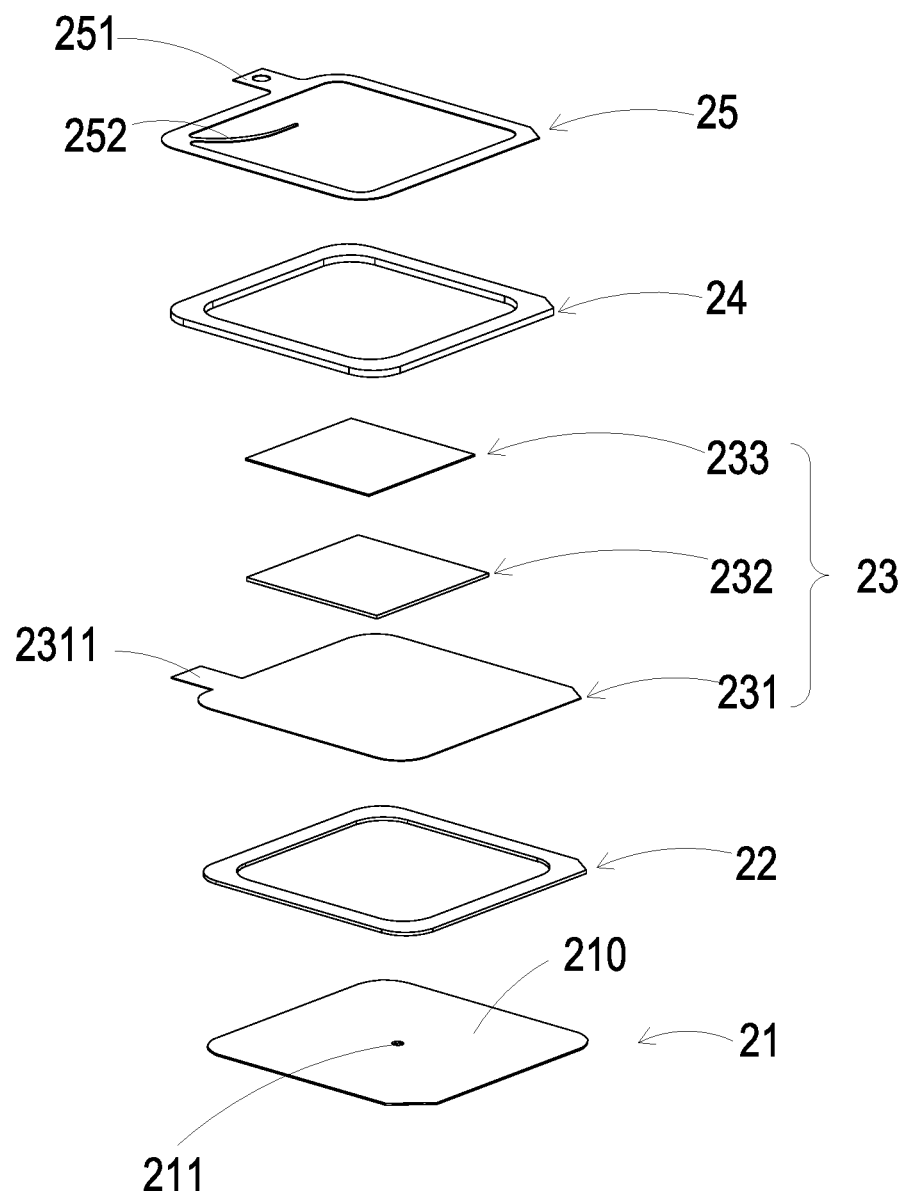
FIG. 6A is a schematic exploded view illustrating the piezoelectric actuator of the gas detection module of the present disclosure.
Figure 6B:
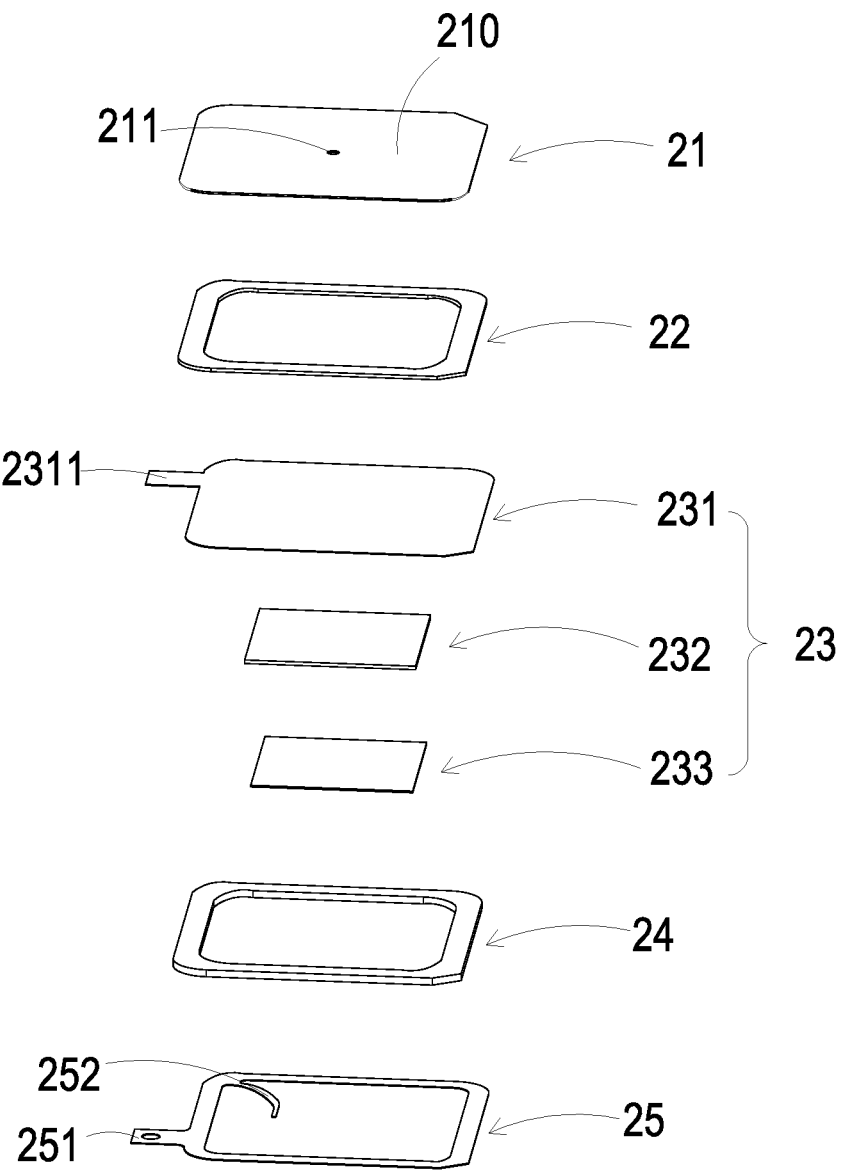
FIG. 6B is a schematic exploded view illustrating the piezoelectric actuator of the gas detection module of the present disclosure and taken from another perspective angle.

Please refer to FIGS. 6A and 6B. In the embodiment, the piezoelectric actuator 2 includes a gas-injection plate 21, a chamber frame 22, an actuator element 23, an insulation frame 24 and a conductive frame 25.

In the embodiment, the gas-injection plate 21 is made by a flexible material and includes a suspension plate 210 and a hollow aperture 211. The suspension plate 210 is a sheet structure and permitted to undergo a bending deformation. Preferably but not exclusively, the shape and the size of the suspension plate 210 are corresponding to an inner edge of the gas-guiding-component loading region 15. The shape of the suspension plate 210 is one selected from the group consisting of a square, a circle, an ellipse, a triangle and a polygon. The hollow aperture 211 passes through a center of the suspension plate 210, so as to allow the gas to flow through.

The chamber frame 22 is carried and stacked on the gas-injection plate 21. In addition, the shape of the chamber frame 22 is corresponding to the gas-injection plate 21. The actuator element 23 is carried and stacked on the chamber frame 22. A resonance chamber 26 is collaboratively defined by the actuator element 23, the chamber frame 22 and the suspension plate 210 and formed among the actuator element 23, the chamber frame 22 and the suspension plate 210. The insulation frame 24 is carried and stacked on the actuator element 23 and the appearance of the insulation frame 24 is similar to that of the chamber frame 22. The conductive frame 25 is carried and stacked on the insulation frame 24, and the appearance of the conductive frame 25 is similar to that of the insulation frame 24. In addition, the conductive frame 25 includes a conducting pin 251 and a conducting electrode 252. The conducting pin 251 is extended outwardly from an outer edge of the conductive frame 25, and the conducting electrode 252 is extended inwardly from an inner edge of the conductive frame 25. Moreover, the actuator element 23 further includes a piezoelectric carrying plate 231, an adjusting resonance plate 232 and a piezoelectric plate 233. The piezoelectric carrying plate 231 is carried and stacked on the chamber frame 22. The adjusting resonance plate 232 is carried and stacked on the piezoelectric carrying plate 231. The piezoelectric plate 233 is carried and stacked on the adjusting resonance plate 232. The adjusting resonance plate 232 and the piezoelectric plate 233 are accommodated in the insulation frame 24. The conducting electrode 252 of the conductive frame 25 is electrically connected to the piezoelectric plate 233. In the embodiment, the piezoelectric carrying plate 231 and the adjusting resonance plate 232 are made by a conductive material. The piezoelectric carrying plate 231 includes a piezoelectric pin 2311. The piezoelectric pin 2311 and the conducting pin 251 are electrically connected to a driving circuit (not shown) of the driving circuit board 3, so as to receive a driving signal, such as a driving frequency and a driving voltage. In that, a loop is formed by the piezoelectric pin 2311, the piezoelectric carrying plate 231, the adjusting resonance plate 232, the piezoelectric plate 233, the conducting electrode 252, the conductive frame 25 and the conducting pin 251 for the driving signal. Moreover, the insulation frame 24 is insulated between the conductive frame 25 and the actuator element 23, so as to avoid the occurrence of a short circuit. Thereby, the driving signal is transmitted to the piezoelectric plate 233. After receiving the driving signal such as the driving frequency and the driving voltage, the piezoelectric plate 233 deforms due to the piezoelectric effect, and the piezoelectric carrying plate 231 and the adjusting resonance plate 232 are further driven to generate the bending deformation in the reciprocating manner.

As described above, the adjusting resonance plate 232 is located between the piezoelectric plate 233 and the piezoelectric carrying plate 231 and served as a buffer between the piezoelectric plate 233 and the piezoelectric carrying plate 231. Thereby, the vibration frequency of the piezoelectric carrying plate 231 is adjustable. Basically, the thickness of the adjusting resonance plate 232 is greater than the thickness of the piezoelectric carrying plate 231, and the thickness of the adjusting resonance plate 232 is adjustable, thereby adjusting the vibration frequency of the actuator element 23.

Please refer to FIGS. 6A, 6B, 6C and FIG. 7A. In the embodiment, the gas-injection plate 21, the chamber frame 22, the actuator element 23, the insulation frame 24 and the conductive frame 25 are stacked and positioned in the gas-guiding-component loading region 15 sequentially. The piezoelectric actuator 2 is disposed and positioned within the gas-guiding-component loading region 15, and the bottom of the piezoelectric actuator 2 is disposed and fixed on the positioning protrusions 15b for supporting and positioning. Thereby, a plurality of vacant spaces 212 are defined between the suspension plate 210 of the piezoelectric actuator 2 and an inner edge of the gas-guiding-component loading region 15. The vacant spaces 212 are surrounding the periphery of the piezoelectric actuator 2 for gas flowing.

Figure 7A:
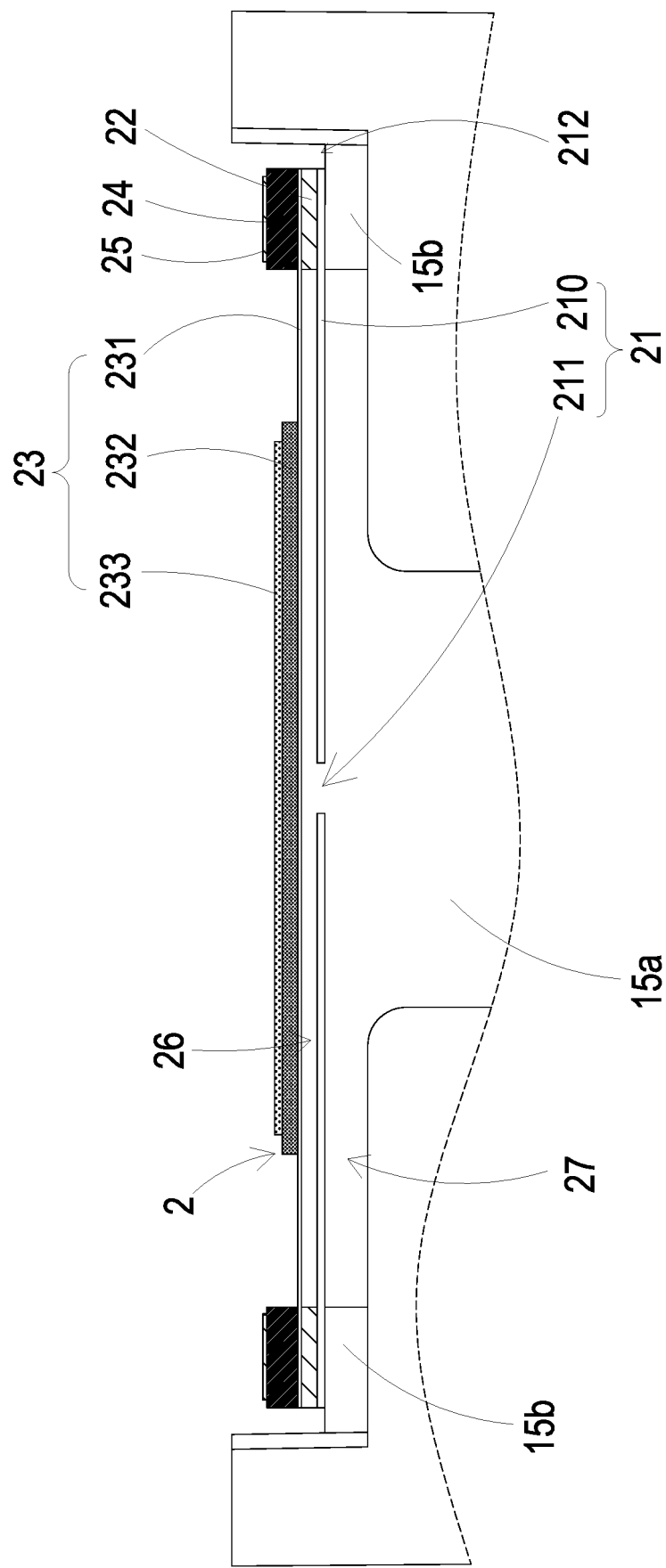
FIG. 7A is a schematic cross-sectional view illustrating the piezoelectric actuator accommodated in the gas-guiding-component loading region of the gas detection module of the present disclosure.

Please refer to FIG. 7A. A flowing chamber 27 is formed between the gas-injection plate 21 and the bottom surface of the gas-guiding-component loading region 15. The flowing chamber 27 is in fluid communication with the resonance chamber 26 among the actuator element 23, the chamber frame 22 and the suspension plate 210 through the hollow aperture 211 of the gas-injection plate 21. By controlling the vibration frequency of the gas in the resonance chamber 26 to be close to the vibration frequency of the suspension plate 210, the Helmholtz resonance effect is generated between the resonance chamber 26 and the suspension plate 210, and thereby the efficiency of gas transportation is improved.

Figure 7B:
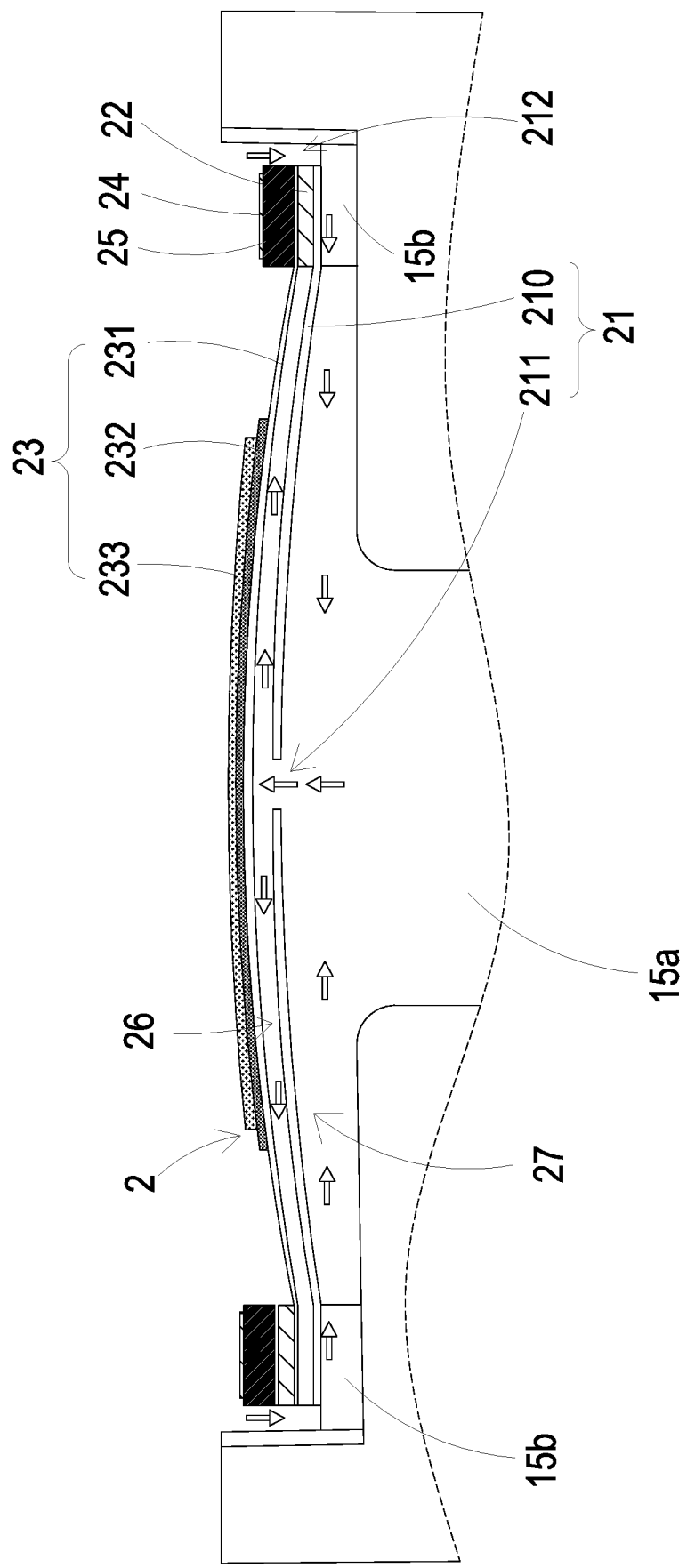
FIGS. 7B and 7C schematically illustrate the actions of the piezoelectric actuator of FIG. 7A.
Figure 7C:
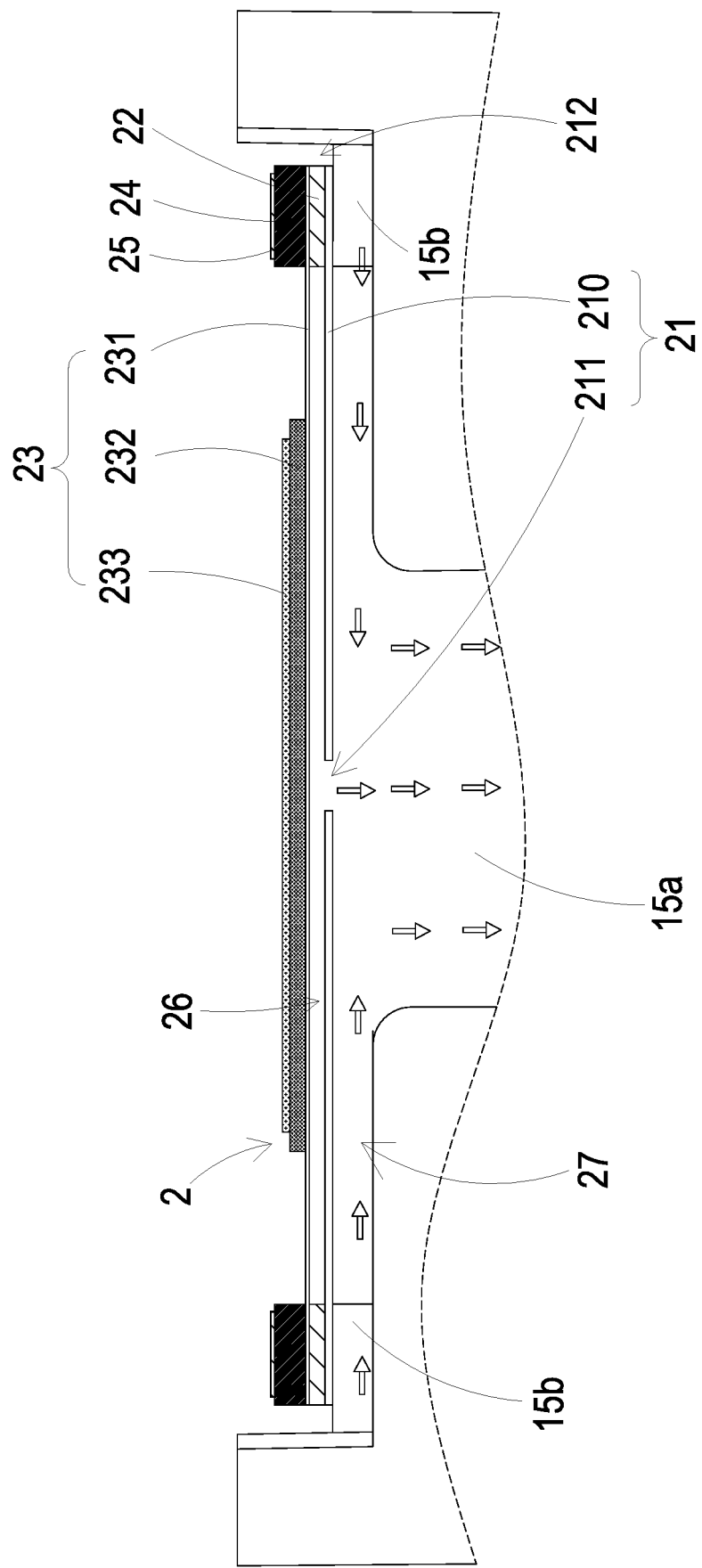

FIGS. 7B and 7C schematically illustrate the actions of the piezoelectric actuator of FIG. 7A. Please refer to FIG. 7B. When the piezoelectric plate 233 is moved away from the bottom surface of the gas-guiding-component loading region 15, the suspension plate 210 of the gas-injection plate 21 is moved away from the bottom surface of the gas-guiding-component loading region 15. In that, the volume of the flowing chamber 27 is expanded rapidly, the internal pressure of the flowing chamber 27 is decreased to form a negative pressure, and the gas outside the piezoelectric actuator 2 is inhaled through the vacant spaces 212 and enters the resonance chamber 26 through the hollow aperture 211. Consequently, the pressure in the resonance chamber 26 is increased to generate a pressure gradient. Further as shown in FIG. 7C, when the suspension plate 210 of the gas-injection plate 21 is driven by the piezoelectric plate 233 to move towards the bottom surface of the gas-guiding-component loading region 15, the gas in the resonance chamber 26 is discharged out rapidly through the hollow aperture 211, and the gas in the flowing chamber 27 is compressed. In that, the converged gas close to an ideal gas state of the Benulli's law is quickly and massively ejected out of the flowing chamber 27 and guided into the ventilation hole 15a of the gas-guiding-component loading region 15. By repeating the above actions shown in FIG. 7B and FIG. 7C, the piezoelectric plate 233 is driven to generate the bending deformation and vibrate in a reciprocating manner. Moreover, according to the principle of inertia, since the gas pressure inside the resonance chamber 26 after exhausting is lower than the equilibrium gas pressure, the gas is introduced into the resonance chamber 26 again. Moreover, the vibration frequency of the gas in the resonance chamber 26 is controlled to be close to the vibration frequency of the piezoelectric plate 233, so as to generate the Helmholtz resonance effect to achieve the gas transportation at high speed and in large quantities.

Figure 8A:
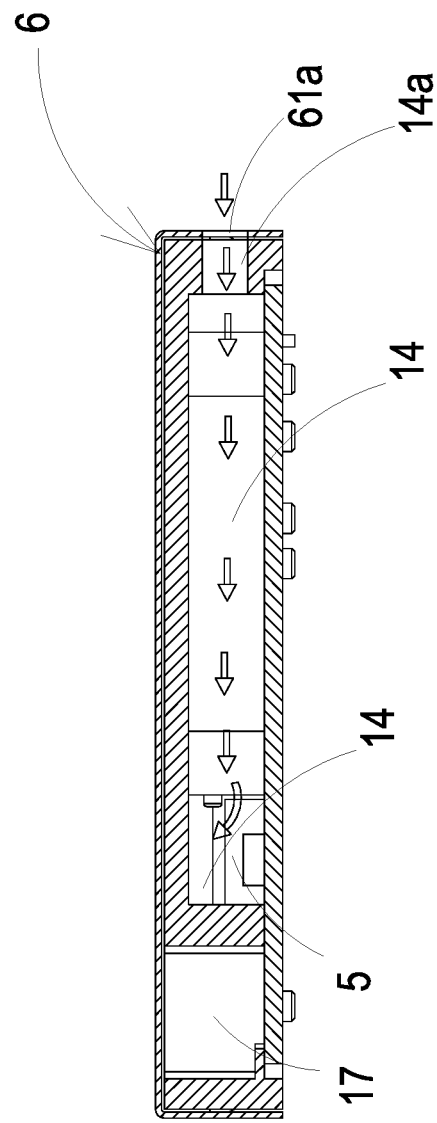
FIGS. 8A to 8C schematically illustrate gas flowing paths of the gas detection module.
Figure 8B:
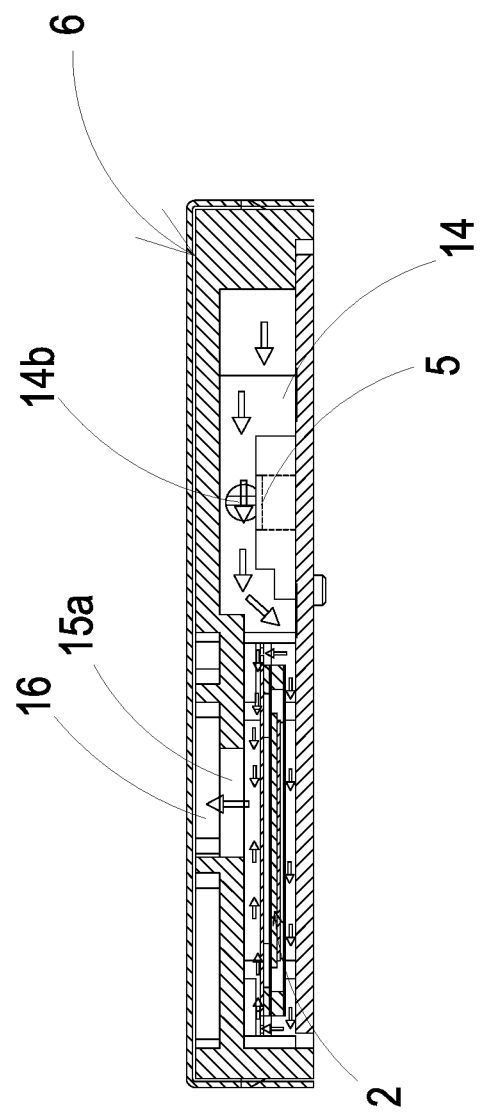
Figure 8C:
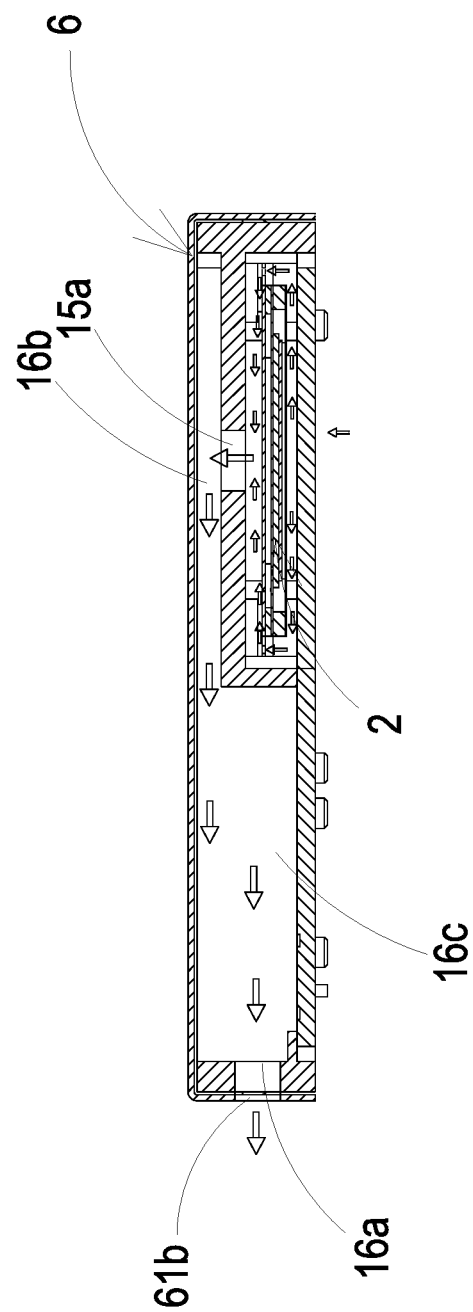

Please refer to FIGS. 8A to 8C. FIGS. 8A to 8C schematically illustrate gas flowing paths of the gas detection module. Firstly, as shown in FIG. 8A, the gas is inhaled through the inlet opening 61a of the outer cover 6, flows into the gas-inlet groove 14 of the base 1 through the gas-inlet 14a, and is transported to the position of the particle sensor 5. Further as shown in FIG. 8B, the piezoelectric actuator 2 is enabled continuously to inhale the gas in the inlet path, and it facilitates the gas to be introduced rapidly, flow stably, and be transported above the particle sensor 5. At this time, a projecting light beam emitted from the laser component 4 passes through the transparent window 14b to irritate the suspended particles contained in the gas flowing above the particle sensor 5 in the gas-inlet groove 14. When the suspended particles contained in the gas are irradiated to generate scattered light spots, the scattered light spots are received and calculated by the particle sensor 5 for obtaining related information about the sizes and the concentration of the suspended particles contained in the gas. Moreover, the gas above the particle sensor 5 is continuously driven and transported by the piezoelectric actuator 2, flows into the ventilation hole 15a of the gas-guiding-component loading region 15, and is transported to the first section 16b of the gas-outlet groove 16. As shown in FIG. 8C, after the gas flows into the first section 16b of the gas-outlet groove 16, the gas is continuously transported into the first section 16b by the piezoelectric actuator 2, and the gas in the first section 16b is pushed to the second section 16c. Finally, the gas is discharged out through the gas-outlet 16a and the outlet opening 61b.

Figure 9:
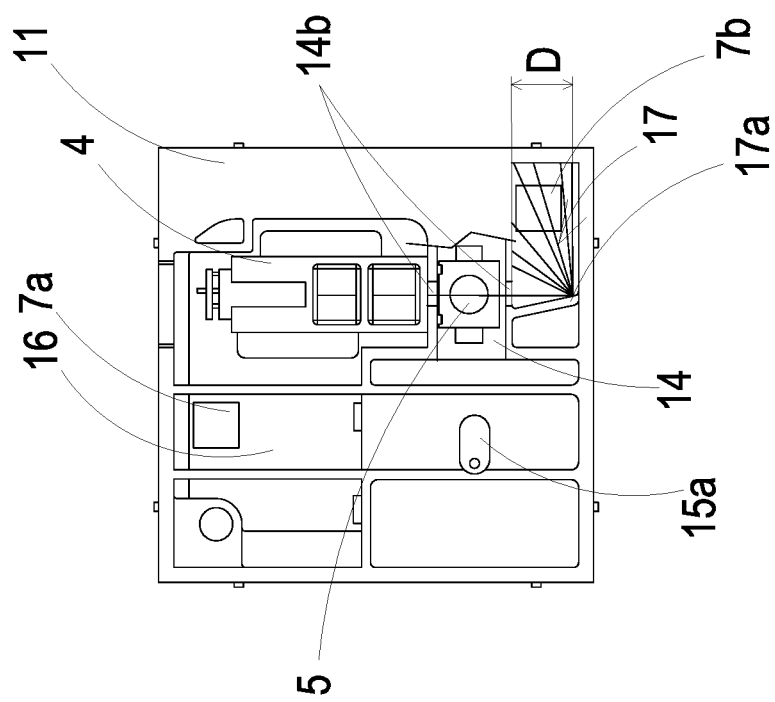
FIG. 9 schematically illustrates a light beam path emitted from the laser component of the gas detection module of the present disclosure.

As shown in FIG. 9, the base 1 further includes a light trapping region 17. The light trapping region 17 is hollowed out from the first surface 11 to the second surface 12 and spatially corresponds to the laser loading region 13. In the embodiment, the light trapping region 17 is corresponding to the transparent window 14b so that the light beam emitted by the laser component 4 is projected into the light trapping region 17. The light trapping region 17 includes a light trapping structure 17a having an oblique cone surface. The light trapping structure 17a spatially corresponds to the light beam path emitted from the laser component 4. In addition, the projecting light beam emitted from the laser component 4 is reflected into the light trapping region 17 through the oblique cone surface of the light trapping structure 17a. It prevents the projecting light beam from being reflected to the position of the particle sensor 5. In the embodiment, a light trapping distance D is maintained between the transparent window 14b and a position where the light trapping structure 17a receives the projecting light beam. Preferably but not exclusively, the light trapping distance D is greater than 3 mm. When the light trapping distance D is less than 3 mm, the projecting light beam projected on the light trapping structure 17a is easy to be reflected back to the position of the particle sensor 5 directly due to excessive stray light generated after reflection, and it results in distortion of detection accuracy.

Please refer to FIG. 2C and FIG. 9. The gas detection module 20 of the present disclosure is not only utilized to detect the suspended particles in the gas, but also further utilized to detect the characteristics of the introduced gas, such as detecting formaldehyde, ammonia, carbon monoxide, carbon dioxide, oxygen, ozone, etc. In the embodiment, the gas detection module 20 further includes a first volatile-organic-compound sensor 7a. The first volatile-organic-compound sensor 7a is positioned and disposed on the driving circuit board 3, electrically connected to the driving circuit board 3, and accommodated in the gas-outlet groove 16, so as to detect the gas flowing through the outlet path of the gas-outlet groove 16. Thus, the concentration or the characteristics of volatile organic compounds contained in the gas in the outlet path is detected. In the embodiment, the gas detection module 20 further includes a second volatile-organic-compound sensor 7b. The second volatile-organic-compound sensor 7b is positioned and disposed on the driving circuit board 3, and electrically connected to the driving circuit board 3. In the embodiment, the second volatile-organic-compound sensor 7b is accommodated in the light trapping region 17. Thus, the concentration or the characteristics of volatile organic compounds contained in the gas flowing through the inlet path of the gas-inlet groove 14 and transported into the light trapping region 17 through the transparent window 14b is detected.

As described above, the gas detection module 20 of the present disclosure is designed to have a proper configuration of the laser loading region 13, the gas-inlet groove 14, the gas-guiding-component loading region 15 and the gas-outlet groove 16 on the base 1. The base 1 is further matched with the outer cover 6 and the driving circuit board 3 to achieve the sealing design. In that, the first surface 11 of the base 1 covers the outer cover 6, and the second surface 12 of the base 1 covers the driving circuit board 3, so that the inlet path is collaboratively defined by the gas-inlet groove 14 and the driving circuit board 3, and the outlet path is collaboratively defined by the gas-outlet groove 16, the outer cover 6 and the driving circuit board 3. The gas flowing path is formed in one layer. It facilitates the gas detection module 20 to reduce the thickness of the overall structure.

Figure 10A:
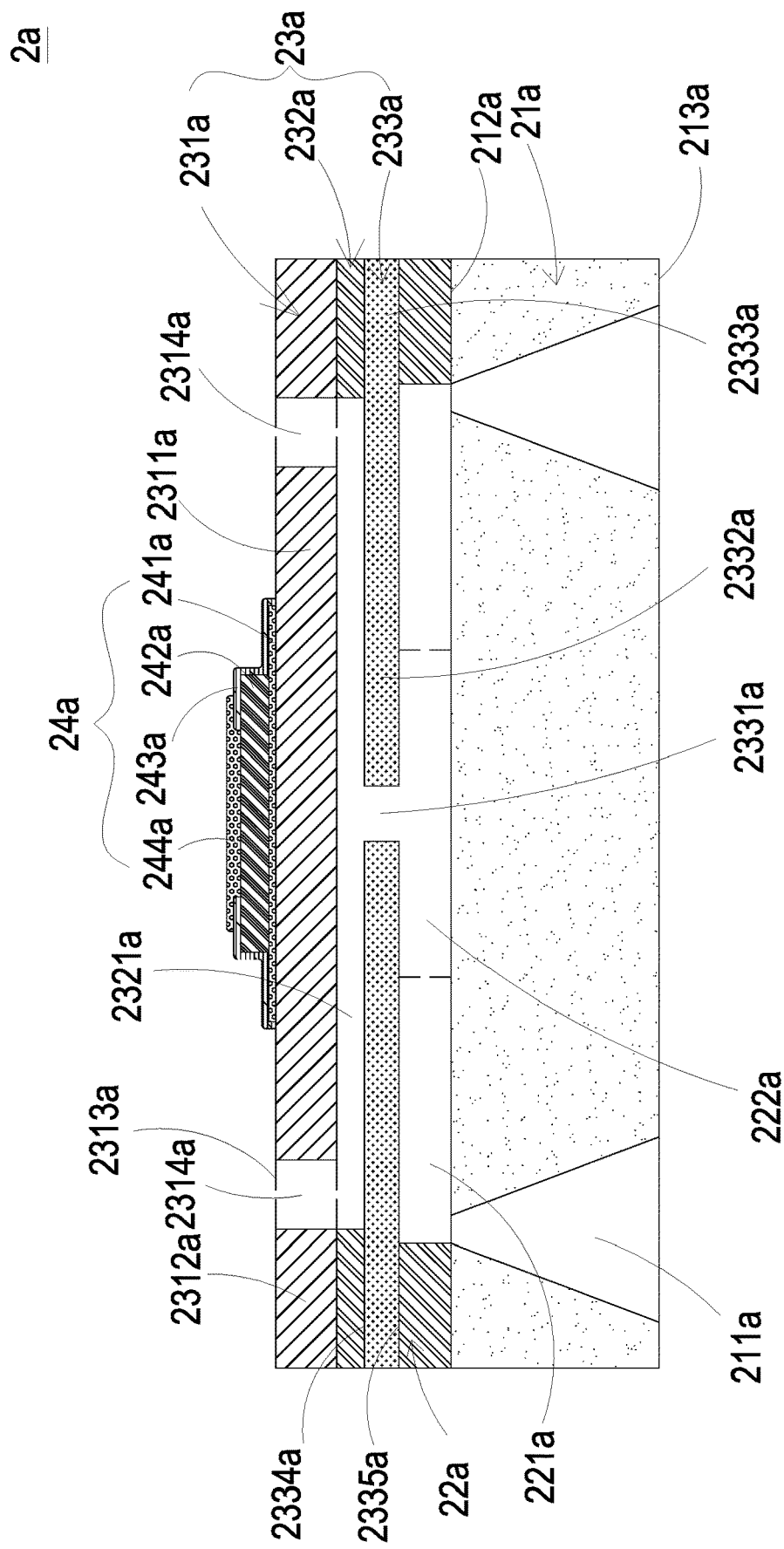
FIG. 10A is a schematic cross-sectional view illustrating a MEMS pump of the gas detection module of the present disclosure.
Figure 10B:
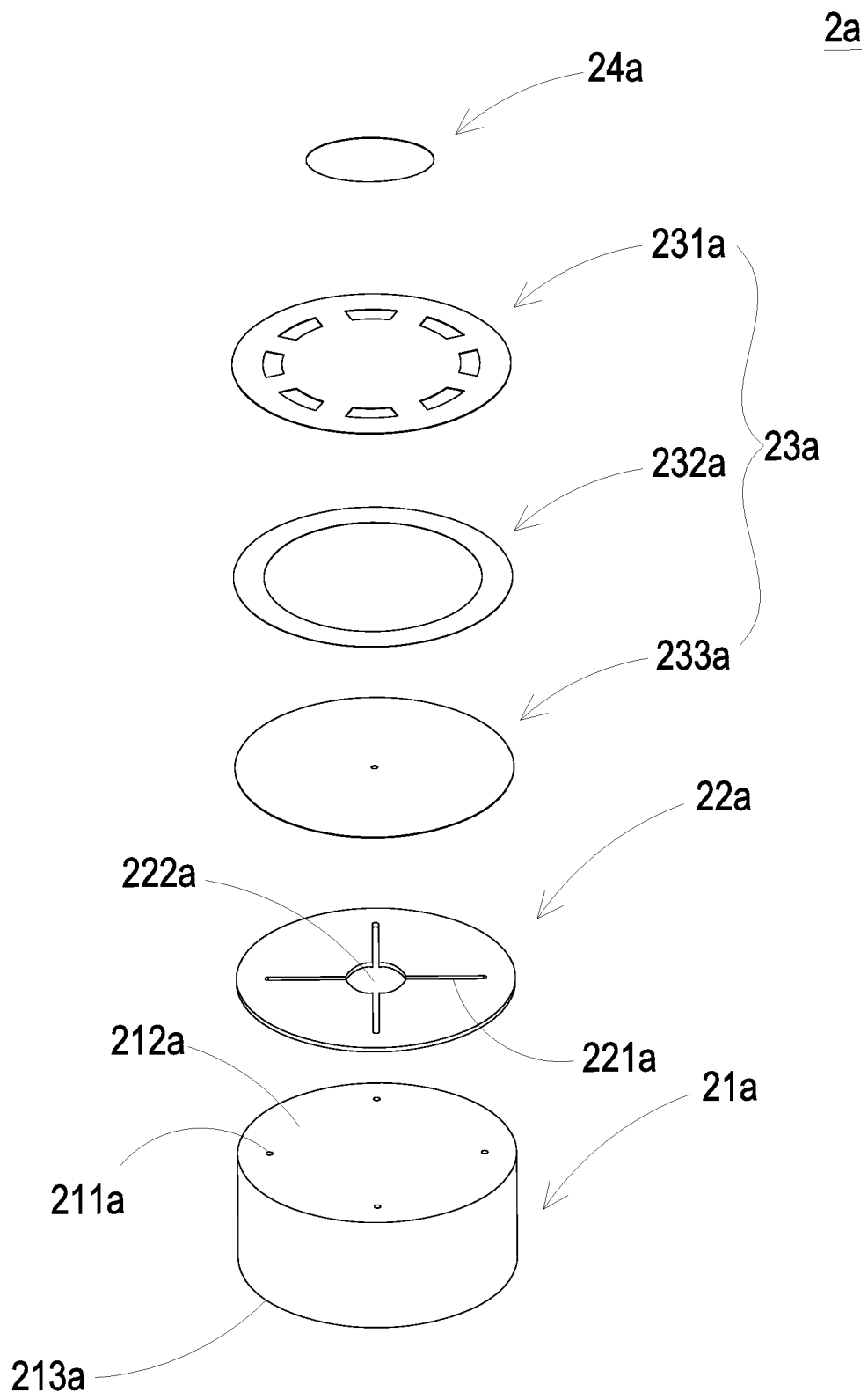
FIG. 10B is a schematic exploded view illustrating the MEMS pump of the gas detection module of the present disclosure.

In addition, the piezoelectric actuator 2 in the above embodiment is replaced with a MEMS pump 2a in another embodiment. Please refer to FIG. 10A and FIG. 10B. The MEMS pump 2a includes a first substrate 21a, a first oxidation layer 22a, a second substrate 23a and a piezoelectric component 24a.

Preferably but not exclusively, the first substrate 21a is a Si wafer and has a thickness ranging from 150 μm to 400 μm. The first substrate 21a includes a plurality of inlet apertures 211a, a first surface 212a and a second surface 213a. In the embodiment, there are four inlet apertures 211a, but the present disclosure is not limited thereto. Each inlet aperture 211a penetrates from the second surface 213a to the first surface 212a. In order to improve the inlet-inflow effect, the plurality of inlet apertures 211a are tapered-shaped, and the size is decreased from the second surface 213a to the first surface 212a.

The first oxidation layer 22a is a silicon dioxide ($SiO_2$) thin film and has the thickness ranging from 10 μm to 20 μm. The first oxidation layer 22a is stacked on the first surface 212a of the first substrate 21a. The first oxidation layer 22a includes a plurality of convergence channels 221a and a convergence chamber 222a. The numbers and the arrangements of the convergence channels 221a and the inlet apertures 211a of the first substrate 21a are corresponding to each other. In the embodiment, there are four convergence channels 221a. First ends of the four convergence channels 221a are in fluid communication with the four inlet apertures 211a of the first substrate 21a, and second ends of the four convergence channels 221a are in fluid communication with the convergence chamber 222a. Thus, after the gas is inhaled through the inlet apertures 211a, the gas flows through the corresponding convergence channels 221a and is converged into the convergence chamber 222a.

Preferably but not exclusively, the second substrate 23a is a silicon on insulator (SOI) wafer, and includes a silicon wafer layer 231a, a second oxidation layer 232a and a silicon material layer 233a. The silicon wafer layer 231a has a thickness ranging from 10 μm to 20 μm, and includes an actuating portion 2311a, an outer peripheral portion 2312a, a plurality of connecting portions 2313a and a plurality of fluid channels 2314a. The actuating portion 2311a is in a circular shape. The outer peripheral portion 2312a is in a hollow ring shape and disposed around the actuating portion 2311a. The plurality of connecting portions 2313a are connected between the actuating portion 2311a and the outer peripheral portion 2312a, respectively, so as to connect the actuating portion 2311a and the outer peripheral portion 2312a for elastically supporting. The plurality of fluid channels 2314a are disposed around the actuating portion 2311a and located between the connecting portions 2313a.

The second oxidation layer 232a is a silicon monoxide (SiO) layer and has a thickness ranging from 0.5 μm to 2 μm. The second oxidation layer 232a is formed on the silicon wafer layer 231a and in a hollow ring shape. A vibration chamber 2321a is collaboratively defined by the second oxidation layer 232a and the silicon wafer layer 231a. The silicon material layer 233a is in a circular shape, disposed on the second oxidation layer 232a and bonded to the first oxidation layer 22a. The silicon material layer 233a is a silicon dioxide ($SiO_2$) thin film and has a thickness ranging from 2 μm to 5 μm. In the embodiment, the silicon material layer 233a includes a through hole 2331a, a vibration portion 2332a, a fixing portion 2333a, a third surface 2334a and a fourth surface 2335a. The through hole 2331a is formed at a center of the silicon material layer 233a. The vibration portion 2332a is disposed around the through hole 2331a and vertically corresponds to the vibration chamber 2321a. The fixing portion 2333a is disposed around the vibration portion 2332a and located at a peripheral region of the silicon material layer 233a. The silicon material layer 233a is fixed on the second oxidation layer 232a through the fixing portion 2333a. The third surface 2334a is connected to the second oxidation layer 232a. The fourth surface 2335a is connected to the first oxidation layer 22a. The piezoelectric component 24a is stacked on the actuating portion 2311a of the silicon wafer layer 231a.

The piezoelectric component 24a includes a lower electrode layer 241a, a piezoelectric layer 242a, an insulation layer 243a and an upper electrode layer 244a. The lower electrode layer 241a is stacked on the actuating portion 2311a of the silicon wafer layer 231a. The piezoelectric layer 242a is stacked on the lower electrode layer 241a. The piezoelectric layer 242a and the lower electrode layer 241a are electrically connected through the contact area thereof. In addition, the width of the piezoelectric layer 242a is less than the width of the lower electrode layer 241a, so that the lower electrode layer 241a is not completely covered by the piezoelectric layer 242a. The insulation layer 243a is stacked on a partial surface of the piezoelectric layer 242a and a partial surface of the lower electrode layer 241a, which is uncovered by the piezoelectric layer 242a. The upper electrode layer 244a is stacked on the insulation layer 243a and a remaining surface of the piezoelectric layer 242a without the insulation layer 243a disposed thereon, so that the upper electrode layer 244a is contacted and electrically connected with the piezoelectric layer 242a. At the same time, the insulation layer 243a is used for insulation between the upper electrode layer 244a and the lower electrode layer 241a, so as to avoid the short circuit caused by direct contact between the upper electrode layer 244a and the lower electrode layer 241a.

Figure 11A:
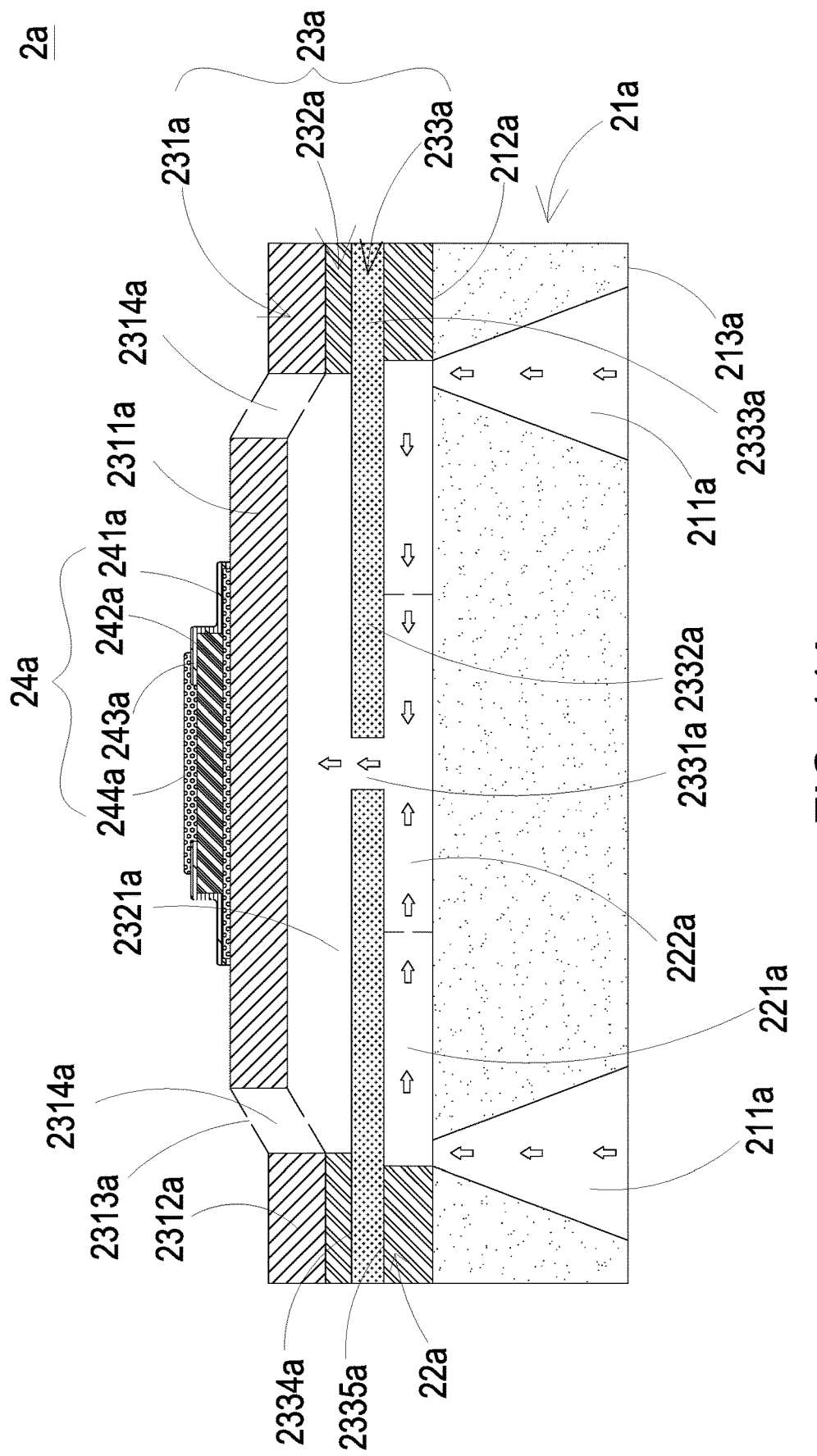
FIGS. 11A to 11C schematically illustrate the actions of the MEMS pump of the gas detection module of the present disclosure.
Figure 11B:
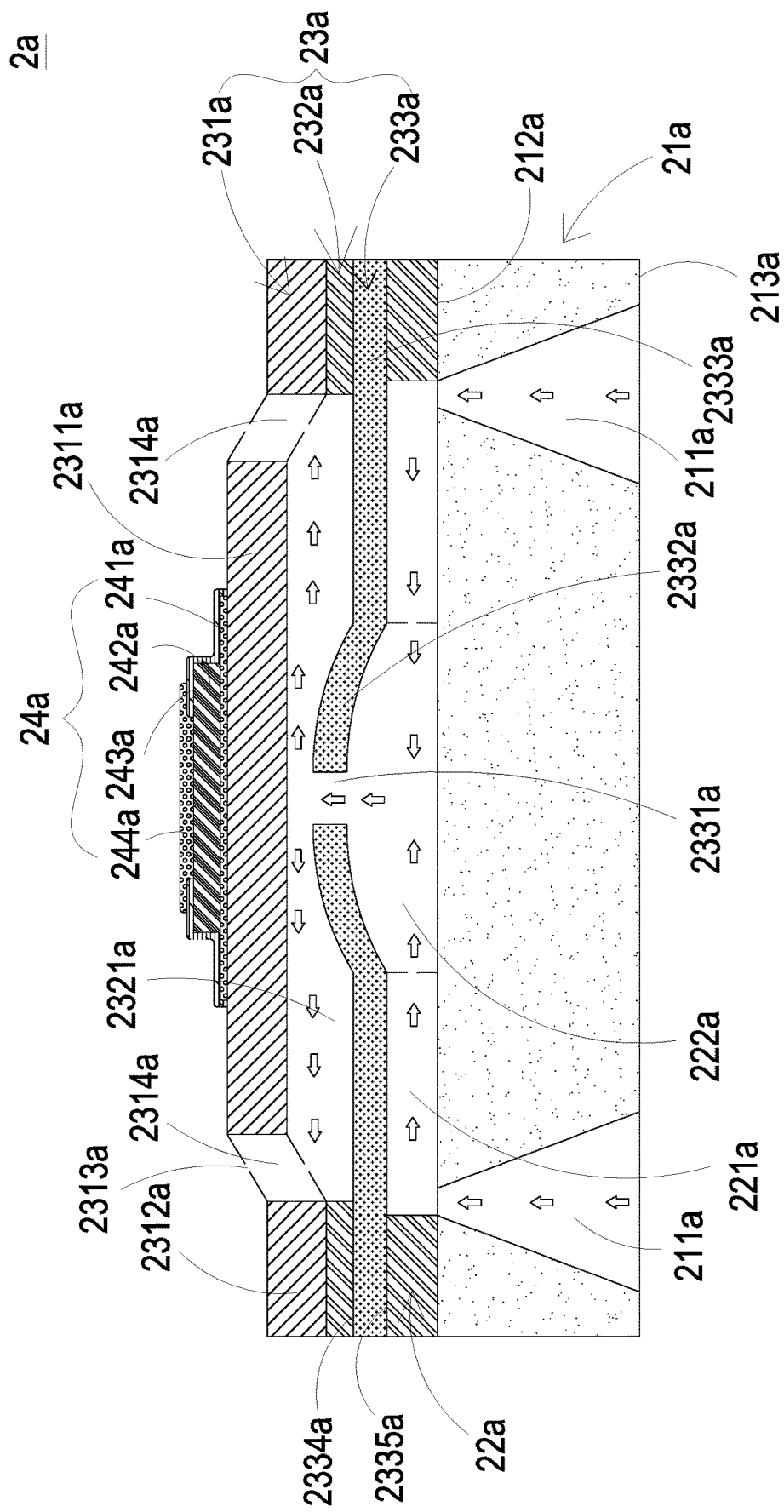
Figure 11C:
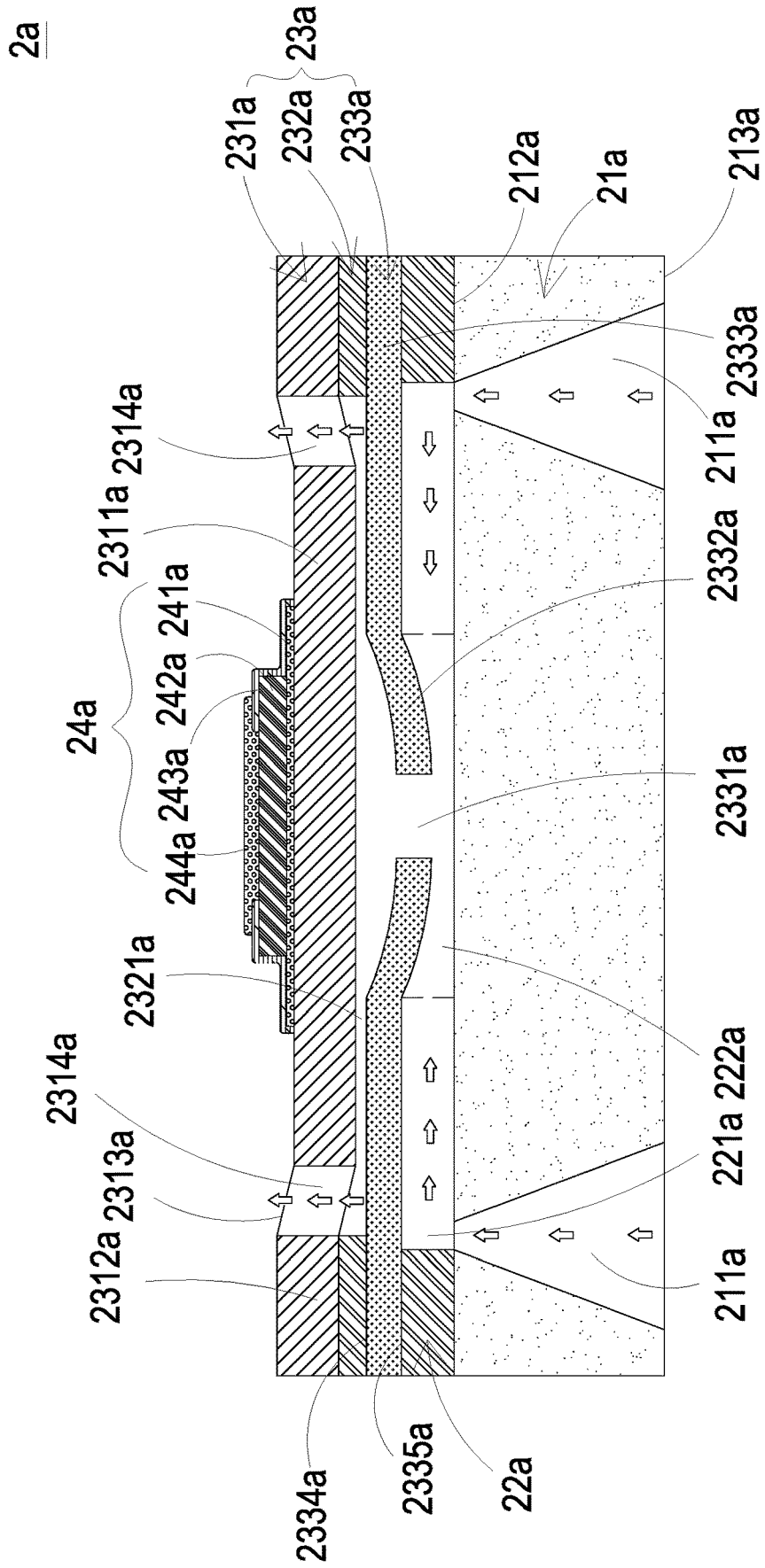

Please refer to FIGS. 11A to 11C. FIGS. 11A to 11C schematically illustrate the actions of the MEMS pump. As shown in FIG. 11A, a driving voltage and a driving signal (not shown) transmitted from the driving circuit board 3 are received by the lower electrode layer 241a and the upper electrode layer 244a of the piezoelectric component 24a, and further transmitted to the piezoelectric layer 242a. After the piezoelectric layer 242a receives the driving voltage and the driving signal, the deformation of the piezoelectric layer 242a is generated due to the influence of the reverse piezoelectric effect. In that, the actuating portion 2311a of the silicon wafer layer 231a is driven to displace. When the piezoelectric component 24a drives the actuating portion 2311a to move upwardly, the actuating portion 2311a is separated away from the second oxidation layer 232a to increase the distance therebetween. In that, the volume of the vibration chamber 2321a of the second oxidation layer 232a is expended rapidly, the internal pressure of the vibration chamber 2321a is decreased to form a negative pressure, and the gas in the convergence chamber 222a of the first oxidation layer 22a is inhaled into the vibration chamber 2321a through the through hole 2331a. Further as shown in FIG. 11B, when the actuating portion 2311a is driven by the piezoelectric component 24a to move upwardly, the vibration portion 2332a of the silicon material layer 233a is moved upwardly due to the influence of the resonance principle. When the vibration portion 2332a is displaced upwardly, the space of the vibration chamber 2321a is compressed and the gas in the vibration chamber 2321a is pushed to move to the fluid channels 2314a of the silicon wafer layer 231a. In that, the gas flows upwardly through the fluid channels 2314a and is discharged out. Moreover, when the vibration portion 2332a is displaced upwardly to compress the vibration chamber 2321a, the volume of the convergence chamber 222a is expended due to the displacement of the vibration portion 2332a, the internal pressure of the convergence chamber 222a is decreased to form a negative pressure, and the gas outside the MEMS pump 2a is inhaled into the convergence chamber 222a through the inlet apertures 211a. As shown in FIG. 11C, when the piezoelectric component 24a is enabled to drive the actuating portion 2311a of the silicon wafer layer 231a to displace downwardly, the gas in the vibration chamber 2321a is pushed to flow to the fluid channels 2314a, and is discharged out. At the same time, the vibration portion 2332a of the silicon material layer 233a is driven by the actuating portion 2311a to displace downwardly, and the gas in the convergence chamber 222a is compressed to flow to the vibration chamber 2321a. Thereafter, when the piezoelectric component 24a drives the actuating portion 2311a to displace upwardly, the volume of the vibration chamber 2321a is greatly increased, and then there is a higher suction force to inhale the gas into the vibration chamber 2321a. By repeating the above actions, the actuating portion 2311a is continuously driven by the piezoelectric component 24a to displace upwardly and downwardly, and further to drive the vibration portion 2332a to displace upwardly and downwardly. By changing the internal pressure of the MEMS pump 2a, the gas is inhaled and discharged continuously, thereby achieving the actions of the MEMS pump 2a.

From the above descriptions, the present disclosure provides an external gas detecting device. With the gas detection module embedded in the external gas detecting device, the air quality around the user is detected at any time, and the air quality information is transmitted to the external transmission device in real time. Thus, the gas detection information and the alarm are provided. It is very industrially usable and inventive.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. An external gas detecting device, comprising:
   a casing;
   a gas detection module disposed in the casing and detecting a gas transported into the casing to generate a gas information; and
   an external connector connected to and disposed on the casing, wherein the external connector includes a plug, and can be plugged in an external receptacle, which is used to be connected to an external power supply so as to enable the gas detection module, and is used to transmit the gas information so as to achieve the outward transmission of the gas information, wherein the gas detection module comprises a base, a piezoelectric actuator, a driving circuit board, a laser component, a particle sensor and an outer cover, wherein the base comprises:
   a first surface;
   a second surface opposite to the first surface; and
   a gas-guiding-component loading region concavely formed from the second surface and in communication with a gas-inlet groove,
   wherein the piezoelectric actuator is accommodated in the gas-guiding-component loading region, the driving circuit board covers and attached to the second surface of the base, the laser component is positioned and disposed on the driving circuit board, is electrically connected to the driving circuit board, and is accommodated in the laser loading region, the particle sensor is positioned and disposed on the driving circuit board, is electrically connected to the driving circuit board, and is disposed at an orthogonal position, and the outer cover covers the first surface of the base and comprises a side plate.

2. The external gas detecting device according to claim 1, wherein the external connector is one selected from the group consisting of a USB connector, a mini USB connector, a Micro USB connector, a USB Type C connector, an AC adapter, a DC power adapter, a power connector, a terminal connector and combination thereof.

3. The external gas detecting device according to claim 1, wherein the gas detection module comprises:
   the base comprising:
   a laser loading region hollowed out from the first surface to the second surface;
   the gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the lateral wall and is in communication with the laser loading region;
   a ventilation hole penetrates a bottom surface of the gas-guiding-component loading region, and the gas-guiding-component loading region has four positioning protrusions disposed at four corners thereof, respectively; and
   a gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base, wherein a light beam path emitted from the laser component passes through the transparent window and extends in a direction perpendicular to the gas-inlet groove, thereby forming an orthogonal direction with the gas-inlet groove;
   the particle sensor disposed at the orthogonal position where the gas-inlet groove intersects the light beam path of the laser component in the orthogonal direction, so that suspended particles passing through the gas-inlet groove and irradiated by a projecting light beam emitted from the laser component are detected; and
   the side plate of the side plate has an inlet opening spatially corresponding to the gas-inlet and an outlet opening spatially corresponding to the gas-outlet, respectively,
   wherein the first surface of the base is covered with the outer cover, and the second surface of the base is covered with the driving circuit board, so that an inlet path is collaboratively defined by the gas-inlet groove and the driving circuit board, and an outlet path is collaboratively defined by the gas-outlet groove, the outer cover and the driving circuit board, so that the gas is inhaled from the exterior of base by the piezoelectric actuator, transported into the inlet path through the inlet opening, and passes through the particle sensor to detect the concentration of the suspended particles contained in the gas, and the gas transported through the piezoelectric actuator is transported out of the outlet path through the ventilation hole and then discharged through the outlet opening.

4. The external gas detecting device according to claim 3, wherein the base comprises a light trapping region hollowed out from the first surface to the second surface and spatially corresponding to the laser loading region, wherein the light trapping region comprises a light trapping structure having an oblique cone surface and spatially corresponding to the light beam path, wherein a light trapping distance is maintained between the transparent window and a position where the light trapping structure receives the projecting light beam.

5. The external gas detecting device according to claim 4, wherein the light trapping distance is greater than 3 mm.

6. The external gas detecting device according to claim 1, wherein the particle sensor is a PM2.5 sensor.

7. The external gas detecting device according to claim 1, wherein the piezoelectric actuator comprises:
   a gas-injection plate comprising a suspension plate and a hollow aperture, wherein the suspension plate is permitted to undergo a bending deformation, and the hollow aperture is formed at a center of the suspension plate;

a chamber frame carried and stacked on the suspension plate;

an actuator element carried and stacked on the chamber frame for being driven in response to an applied voltage to undergo the bending deformation in a reciprocating manner;

an insulation frame carried and stacked on the actuator element; and a conductive frame carried and stacked on the insulation frame, wherein the gas-injection plate is disposed and fixed on the positioning protrusions of the gas-guiding-component loading region for supporting and positioning, a plurality of vacant spaces surrounding the periphery of the gas-injection plate for gas flowing are defined between the gas-injection plate and an inner edge of the gas-guiding-component loading region, and a flowing chamber is formed between the gas-injection plate and the bottom surface of the gas-guiding-component loading region, wherein a resonance chamber is formed among the actuator element, the chamber frame and the suspension plate, wherein when the actuator element is enabled to drive the gas-injection plate to move in resonance, the suspension plate of the gas-injection plate is driven to generate the bending deformation in a reciprocating manner, the gas is inhaled through the vacant space, flows into the flowing chamber, and is discharged out, so as to achieve gas transportation.

8. The external gas detecting device according to claim 7, wherein the actuator element comprises:
a piezoelectric carrying plate carried and stacked on the chamber frame;
an adjusting resonance plate carried and stacked on the piezoelectric carrying plate; and
a piezoelectric plate carried and stacked on the adjusting resonance plate, wherein the piezoelectric plate is configured to drive the piezoelectric carrying plate and the adjusting resonance plate to generate the bending deformation in the reciprocating manner by the applied voltage.

9. The external gas detecting device according to claim 3, wherein the gas detection module further comprises a first volatile-organic-compound sensor positioned and disposed on the driving circuit board, electrically connected to the driving circuit board, and accommodated in the gas-outlet groove, so as to detect the gas flowing through the outlet path of the gas-outlet groove.

10. The external gas detecting device according to claim 4, wherein the gas detection module further comprises a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

11. The external gas detecting device according to claim 10, wherein the gas is one selected from the group consisting of formaldehyde, ammonia, carbon monoxide, carbon dioxide, oxygen and ozone.

12. The external gas detecting device according to claim 1, wherein the piezoelectric actuator is a microelectromechanical systems pump comprising:

a first substrate having a plurality of inlet apertures, wherein the plurality of inlet apertures are tapered-shaped;

a first oxidation layer stacked on the first substrate, wherein the first oxidation layer comprises a plurality of convergence channels and a convergence chamber, and the plurality of convergence channels are in communication between the convergence chamber and the plurality of inlet apertures;

a second substrate combined with the first substrate and comprising:
a silicon wafer layer, comprising:
an actuating portion being in a circular shape;
an outer peripheral portion being in a hollow ring shape and disposed around the actuating portion;
a plurality of connecting portions connected between the actuating portion and the outer peripheral portion, respectively; and
a plurality of fluid channels disposed around the actuating portion and located between the connecting portions;
a second oxidation layer formed on the silicon wafer layer and being in a hollow ring shape, wherein a vibration chamber is collaboratively defined by the second oxidation layer and the silicon wafer layer; and
a silicon material layer being in a circular shape, disposed on the second oxidation layer and bonded to the first oxidation layer, comprising:
a through hole formed at a center of the silicon material layer;
a vibration portion disposed around the through hole; and
a fixing portion disposed around the vibration portion; and
a piezoelectric component being in a circular shape and stacked on the actuating portion of the silicon wafer layer.

13. The external gas detecting device according to claim 12, wherein the piezoelectric component comprises:
a lower electrode layer;
a piezoelectric layer stacked on the lower electrode layer; and
an insulation layer disposed on a partial surface of the piezoelectric layer and a partial surface of the lower electrode layer; and
an upper electrode layer stacked on the insulation layer and a remaining surface of the piezoelectric layer without the insulation layer disposed thereon, so as to electrically connect with the piezoelectric layer.

14. The external gas detecting device according to claim 1, further comprising a controlling circuit unit, wherein a microprocessor and a communicator are disposed on and electrically coupled with the controlling circuit unit, wherein the microprocessor is configured to control a driving signal of the gas detection module to enable the gas detection module to detect and operate, and convert the gas information of the gas detection module to a detection data for storing, wherein the communicator is configured to receive the detection data transmitted from the microprocessor and externally transmit the detection data to an external transmission device through a communication transmission for storing, and the external transmission device generate a gas detection information and an alarm based on the detection data.

15. The external gas detecting device according to claim 14, wherein the external transmission device is one selected from the group consisting of a cloud system, a portable device and a computer system.

16. The external gas detecting device according to claim 14, wherein the gas detection module and the controlling circuit unit are assembled and electrically connected to each other for forming a gas detecting and transmitting module, and the gas detecting and transmitting module has a length ranging between 35 mm and 55 mm, a width ranging between 10 mm and 35 mm, and a thickness ranging between 1 mm and 7.5 mm.

17. The external gas detecting device according to claim 16, wherein the gas detecting and transmitting module is accommodated in the casing and is covered and protected by the casing, the external connector is exposed to achieve an electrical connection, so that the external gas detecting device is formed, wherein the external gas detecting device has a length ranging between 45 mm and 70 mm, a width ranging between 25 mm and 42 mm, and a thickness ranging between 7 mm and 13 mm.

18. The external gas detecting device according to claim 1, wherein an electric energy is transmitted to the external connector from an external connection device, and a detection data transmitted by a microprocessor is transmitted to the external connection device through the external connector for processing and application, wherein the detection data is further transmitted by the external connection device through the communication transmission to an external transmission device for storing, and the external transmission device generates a gas detection information and an alarm based on the detection data.

19. The external gas detecting device according to claim 18, wherein the external connection device is a mobile device.

20. The external gas detecting device according to claim 18, wherein the controlling circuit unit further comprises a power module, the power module receives the electric energy through a power supply device via a wireless transmission technology for storing the electric energy so as to enable the gas detection module to operate.

* * * * *